United States Patent [19]
Ishizaka et al.

[11] Patent Number: 5,094,816
[45] Date of Patent: Mar. 10, 1992

[54] BIOCHEMICAL ANALYSIS APPARATUS WITH A POSITIONABLE SENSOR

[75] Inventors: Hideo Ishizaka; Shinichi Nakama; Tadashi Uekusa, all of Kanagawa; Yoshio Saito, Saitama; Yukihide Miyata; Takashi Koizumi, both of Kanagawa, all of Japan

[73] Assignee: Fuji Photo Film Co., Ltd., Kanagawa, Japan

[21] Appl. No.: 715,697

[22] Filed: Jun. 17, 1991

Related U.S. Application Data

[63] Continuation of Ser. No. 07/236,492, Aug. 25, 1988, abandoned.

[30] Foreign Application Priority Data

| Aug. 25, 1987 | [JP] | Japan | 62-211139 |
| Aug. 25, 1987 | [JP] | Japan | 62-211140 |
| Nov. 19, 1987 | [JP] | Japan | 62-292592 |
| Nov. 19, 1987 | [JP] | Japan | 62-292593 |
| Nov. 19, 1987 | [JP] | Japan | 62-292594 |
| Nov. 19, 1987 | [JP] | Japan | 62-292595 |
| Nov. 19, 1987 | [JP] | Japan | 62-292597 |
| Dec. 19, 1987 | [JP] | Japan | 62-292596 |

[51] Int. Cl.$^5$ .................. G01N 21/01; G01N 21/86
[52] U.S. Cl. ................. 422/66; 422/56; 422/58; 435/291; 435/808; 436/44; 436/47; 436/169
[58] Field of Search ............. 436/46, 47, 170, 44, 436/169, 805; 356/36; 422/56, 58, 66; 435/291, 808

[56] References Cited

U.S. PATENT DOCUMENTS

3,508,879  4/1970  Findl et al.
4,250,257  2/1981  Lee et al. ............... 436/44

FOREIGN PATENT DOCUMENTS

53-21677    7/1978   Japan.
55-164356  12/1980   Japan.
56-77746    6/1981   Japan.
1049364     7/1963   United Kingdom.

OTHER PUBLICATIONS

Patent Abstracts of Japan, vol. 11, No. 162, JP-A-61 294 368.

*Primary Examiner*—Kenneth M. Schor
*Assistant Examiner*—John Hoffmann
*Attorney, Agent, or Firm*—Sughrue, Mion, Zinn Macpeak & Seas

[57] ABSTRACT

A biochemical analysis apparatus for applying a liquid sample onto a long test film, incubating the sample-applied film portion by an incubator, and measuring the degree of color formation at the sample-applied portion comprises a test film conveyor for continuously conveying at least the part of the long test film inside of the incubator so that a speed v [cm/min.] at which the part of the long test film inside of the incubator is conveyed is expressed as $v = n.l$. The incubator is constituted so that a length L [cm] of the incubator in the direction of conveyance of the long test film satisfies the condition of $L \geq (nt+1).l$, where l [cm] denotes the length of a portion of the long test film necessary for a single step of sample application, t [min.] denotes the incubation time, and n [number/min.] denotes the number of repetitions of sample application per unit time.

2 Claims, 15 Drawing Sheets

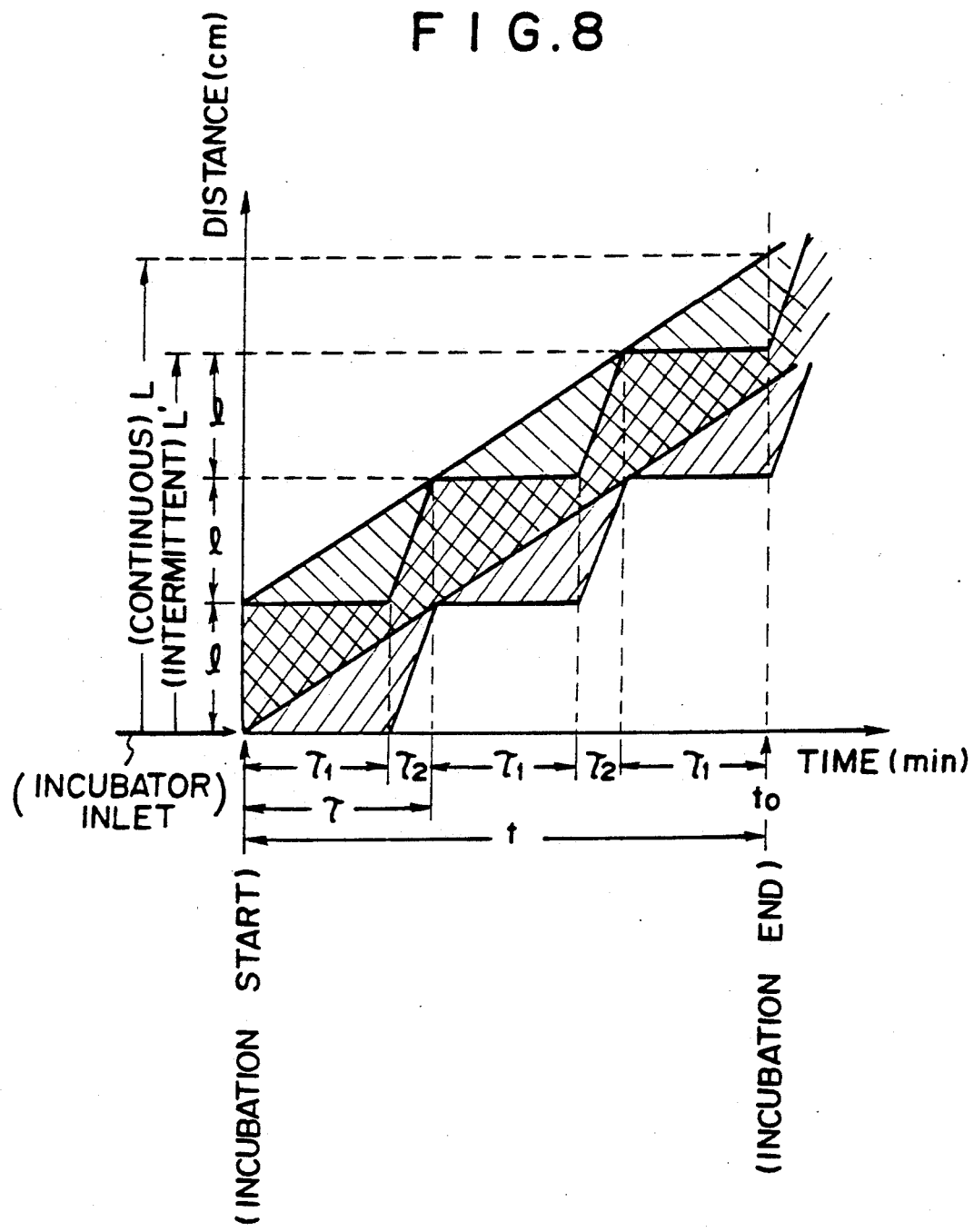

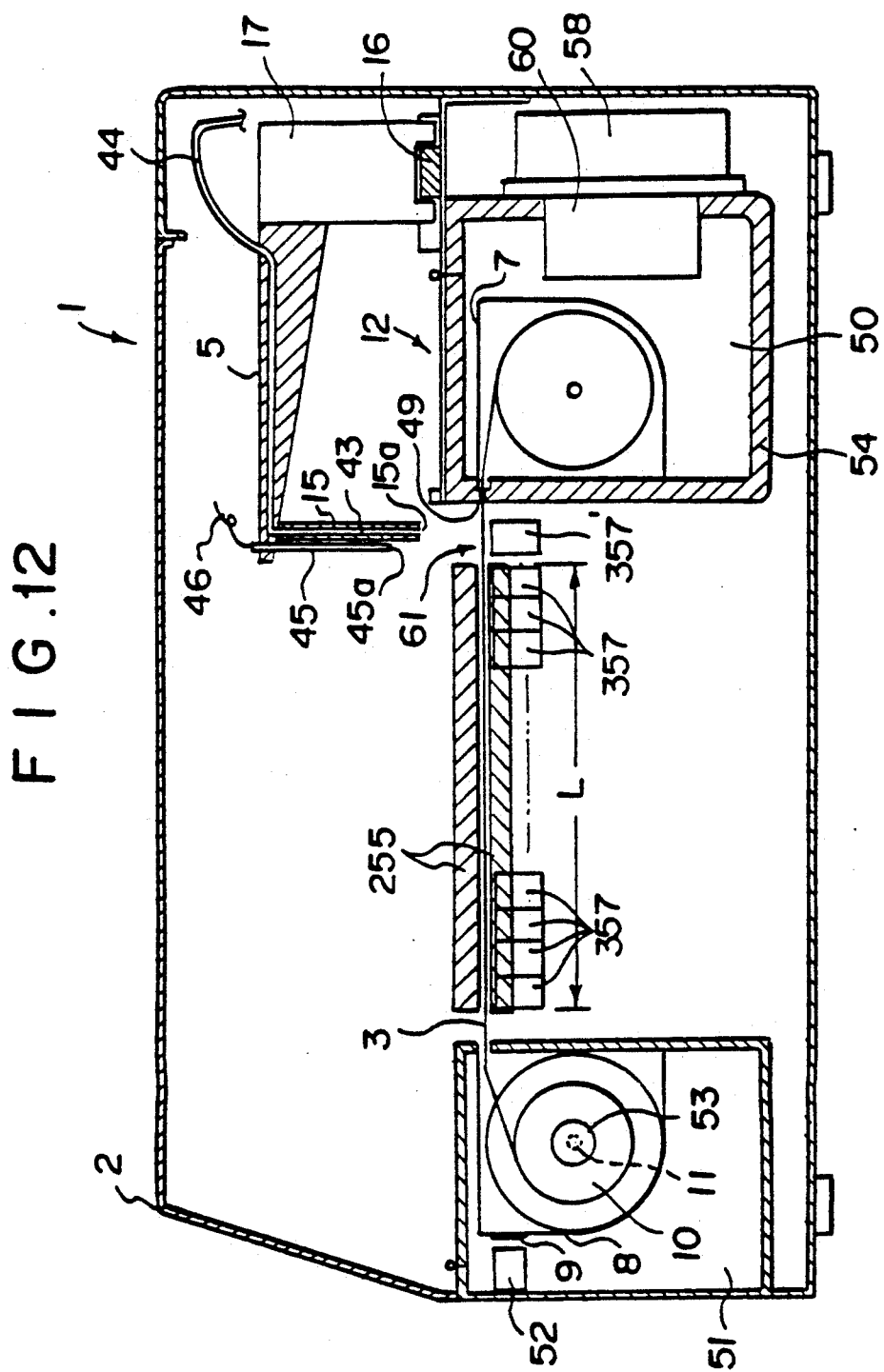

BIOCHEMICAL ANALYSIS APPARATUS WITH A POSITIONABLE SENSOR

This is continuation of application No. 07/236,492 filed Aug. 25, 1988 now abandoned.

BACKGROUND OF THE INVENTION

1. Field of the Invention

This invention relates to a biochemical analysis apparatus for applying a liquid sample to a test film provided with a single reagent layer or a plurality of reagent layers, maintaining the test film at a predetermined temperature (i.e. carrying out incubation) for a predetermined time, and measuring the degree of color formation given rise to by a reaction of the reagent with the liquid sample during or after the incubation. This invention particularly relates to a biochemical analysis apparatus suitable for quick processing.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a liquid sample simply by applying a droplet of the liquid sample. With the chemical analysis slide, it is possible to analyze a liquid sample more simply and more quickly than with the conventional wet type analysis method. Therefore, the use of the chemical analysis slide is desirable particularly in medical organizations, research laboratories, or the like where many samples are to be analyzed.

In order to quantitatively analyze a chemical constituent or the like contained in a liquid sample by use of the chemical analysis slide, a measured amount of the liquid sample is put on the chemical analysis slide and is maintained at a predetermined temperature (i.e. incubated) for a predetermined time in an incubator to cause a color reaction. The chemical analysis slide is then exposed to measuring light having a wavelength selected in advance in accordance with the combination of the constituent of the liquid sample with a reagent contained in the reagent layer of the chemical analysis slide, and the light reflected by the chemical analysis slide is measured in terms of the optical density.

In the medical organizations, research laboratories or the like in which many liquid samples are to be analyzed, it is desirable that the analysis be conducted automatically and sequentially. To satisfy this need, there have been proposed various chemical analysis apparatuses for carrying out sample analysis automatically and sequentially by use of the aforesaid chemical analysis slides. One of such chemical analysis apparatuses is disclosed in, for example, Japanese Unexamined Patent Publication No. 56(1981)-77746. Also, as a means for analyzing liquid samples automatically and sequentially, there has been proposed in, for example, U.S. Pat. No. 3,526,480 an apparatus wherein a long tape-like test film containing a reagent is utilized instead of the aforesaid chemical analysis slides, and sample application, incubation and measurement are carried out sequentially by pulling out the test film.

With the technique wherein a single chemical analysis slide is used for a single measurement, many chemical analysis slides must be processed for automatically and sequentially carrying out the analysis of liquid samples, and therefore the apparatus becomes complicated, large and expensive. On the other hand, the technique wherein the long tape-like test film is used is advantageous for carrying out measurement automatically and sequentially. However, after the liquid sample is sequentially applied to the test film, a long time is required for the incubation in the incubator. Therefore, for example, the test film must be stopped for a predetermined time with the sample-applied portion thereof accommodated in the incubator, or the conveyance speed for the test film must be decreased after the sample-applied portion is inserted into the incubator.

SUMMARY OF THE INVENTION

The primary object of the present invention is to provide a biochemical analysis apparatus which is made simple, small and cheap by employing the system utilizing a long tape-like test film advantageous for carrying out measurement automatically and sequentially, and wherein sample application, incubation and measurement of the long test film are carried out sequentially without the incubation time obstructing quick processing.

Another object of the present invention is to provide a biochemical analysis apparatus which maximizes the use efficiency of a long test film.

The present invention provides a first biochemical analysis apparatus comprising:

i) a sample accommodating means for accommodating a liquid sample, ii) a test film accommodating means for accommodating a long test film containing a reagent which reacts with said liquid sample to give rise to a change in optical density, iii) a test film conveyance means for sequentially pulling out said long test film accommodated in said test film accommodating means, iv) a sample application means for taking up said liquid sample accommodated in said sample accommodating means and applying a predetermined amount of said liquid sample onto said long test film at the position to which said long test film has been pulled out of said test film accommodating means, v) an incubator for maintaining the sample-applied portion of said long test film at a predetermined temperature for a predetermined time, and vi) a measurement means for irradiating light to said sample-applied portion of said long test film and measuring the optical density given rise to by said reaction during or after the passage of said predetermined time, wherein the a) constituting said test film conveyance means to continuously convey at least the part of said long test film inside of said incubator so that a speed v [cm/min.] at which the part of said long test film inside of said incubator is conveyed is expressed as $$v = n \cdot l,$$

and b) constituting said incubator so that a length L [cm] of said incubator in the direction of conveyance of said long test film satisfies the condition $$L \geq (nt+1) \cdot l,$$

where l [cm] denotes the length of a portion of said long test film necessary for a single step of sample application, t [min.] denotes said predetermined time, and n [number/min.] denotes the number of repetitions of said sample application per unit time.

The present invention also provides a second biochemical analysis apparatus for applying the liquid sample onto the long test film, incubating the sample-applied portion of the long test film by the incubator, and measuring the degree of color formation at the sample-applied portion by the measurement means in the manner as mentioned above, wherein the a) constituting said test film conveyance means to continuously convey at least the part of said long test film inside of said incubator so that a speed v [cm/min.] at which the part of said long test film inside of said incubator is conveyed is expressed as $$V = n \cdot l,$$

b) constituting said incubator so that a length L [cm] of said incubator in the direction of conveyance of said long test film satisfies the condition $$L \geq (nt+1) \cdot l,$$

and c) providing said measurement means so that a distance M [cm] between an inlet of said incubator for said long test film and said measurement means as measured from said inlet of said incubator toward an outlet thereof satisfies the condition $$M = (nt+1) \cdot l,$$

where l [cm] denotes the length of a portion of said long test film necessary for a single step of sample application, t [min.] denotes said predetermined time, and n [number/min.] denotes the number of repetitions of said sample application per unit time.

The present invention further provides a third biochemical analysis apparatus for applying the liquid sample onto the long test film, incubating the sample-applied portion of the long test film by the incubator, and measuring the degree of color formation at the sample-applied portion by the measurement means in the manner as mentioned above, wherein the a) constituting said incubator to have a length in the direction of conveyance of said long test film adapted to accommodation of a plurality of sample-applied portions of said long test film, and b) providing said measurement means moveably along the part of said long test film inside of said incubator for measuring the optical density of a plurality of said sample-applied portions of said long test film inside of said incubator.

The present invention still further provides a fourth biochemical analysis apparatus for applying the liquid sample onto the long test film, incubating the sample-applied portion of the long test film by the incubator, and measuring the degree of color formation at the sample-applied portion by the measurement means in the manner as mentioned above, wherein the a) constituting said incubator to have a length in the direction of conveyance of said long test film adapted to accommodation of a plurality of sample-applied portions of said long test film, and b) providing a plurality of measurement means along the part of said long test film inside of said incubator for measuring the optical density of a plurality of said sample-applied portions of said long test film inside of said incubator.

The present invention also provides a fifth biochemical analysis apparatus for applying the liquid sample onto the long test film, incubating the sample-applied portion of the long test film by the incubator, and measuring the degree of color formation at the sample-applied portion by the measurement means in the manner as mentioned above, wherein the a) constituting said incubator so that a length L [cm] of said incubator in the direction of conveyance of said long test film satisfies the condition $$L \geq 2l \cdot (nt+1),$$

b) providing said measurement means so that a distance M [cm] between an inlet of said incubator for said long test film and said measurement means as measured from said inlet of said incubator toward an outlet thereof satisfies the condition $$l \cdot (nt+1) \leq T_i \, M \leq L - l \cdot (nt+1),$$

where l [cm] denotes the length of a portion of said long test film necessary for a single step of sample application, t [min.] denotes said predetermined time, and n [number/min.] denotes the number of repetitions of said sample application per unit time, and c) constituting said test film conveyance means to continuously reciprocally move at least the part of said long test film inside of said incubator in the length direction of said long test film.

The present invention further provides a sixth biochemical analysis apparatus for applying the liquid sample onto the long test film, incubating the sample-applied portion of the long test film by the incubator, and measuring the degree of color formation at the sample-applied portion by the measurement means in the manner as mentioned above, wherein the a) constituting said test film conveyance means to intermittently convey at least the part of said long test film inside of said incubator by a distance equal to a length l [cm] at one time, and b) constituting said incubator so that a length L [cm] of said incubator in the direction of conveyance of said long test film satisfies the condition $$L \geq [nt+1] \cdot l,$$

where l [cm] denotes the length of a portion of said long test film necessary for a single step of sample application, t [min.] denotes said predetermined time, n [number/min.] denotes the number of repetitions of said sample application per unit time, and [nt+1] denotes the largest integer within the range not larger than nt+1.

The present invention still further provides a seventh biochemical analysis apparatus for applying the liquid sample onto the long test film, incubating the sample-applied portion of the long test film by the incubator, and measuring the degree of color formation at the sample-applied portion by the measurement means in the manner as mentioned above, wherein the a) constituting said test film conveyance means to intermittently convey at least the part of said long test film inside of said incubator by a distance equal to a length l [cm] at one time, b) constituting said incubator so that a length L [cm] of said incubator in the direction of conveyance of said long test film satisfies the condition $$L \geq [nt+1] \cdot l,$$

and c) providing said measurement means so that a distance M [cm] between an inlet of said incubator for said long test film and said measurement means as measured from said inlet of said incubator toward an outlet thereof satisfies the condition $$M = [nt+1] \cdot l,$$

where l [cm] denotes the length of a portion of said long test film necessary for a single step of sample application, t [min.] denotes said predetermined time, n [number/min.] denotes the number of repetitions of said sample application per unit time, and [nt+1] denotes the largest integer within the range not larger than nt+1.

The present invention also provides an eighth biochemical analysis apparatus for applying the liquid sample onto the long test film, incubating the sample-applied portion of the long test film by the incubator, and measuring the degree of color formation at the sample-applied portion by the measurement means in the manner as mentioned above, wherein the a) constituting said incubator so that a length L [cm] of said incubator in the direction of conveyance of said long test film satisfies the condition $$L \geq 2l \cdot [nt+1],$$

b) providing said measurement means so that a distance M [cm] between an inlet of said incubator for said long test film and said measurement means as measured from said inlet of said incubator toward an outlet thereof satisfies the condition $$l \cdot [nt+1] \leq M \leq L - l \cdot [nt+1],$$

and c) constituting said test film conveyance means to intermittently move forward at least the part of said long test film inside of said incubator toward said outlet of said incubator by a distance equal to a length l [cm] at one time, and to reciprocally move at least the part of said long test film inside of said incubator so that said sample-applied portion is moved to the position of said measurement means at the time said optical density is to be measured, where l [cm] denotes the length of a portion of said long test film necessary for a single step of sample application, t [min.] denotes said predetermined time, n [number/min.] denotes the number of repetitions of said sample application per unit time, and [nt+1] denotes the largest integer within the range not larger than nt+1.

With the first and second biochemical analysis apparatuses in accordance with the present invention, in order that the sample-applied portion of the long test film remains in the incubator for the incubation time t [min.] when sample application, incubation and measurement are carried out by continuously conveying the long test film at the speed v [cm/min.], the length L of the incubator may be $$L \geq vt + l \ldots \quad (1)$$

As is clear from Formula (1), the incubation time t [min.] is defined as the time from when the overall portion having the length l [cm] on which a liquid sample has been applied in a single step of sample application is conveyed into the incubator to when the portion having the length l [cm] is at least partially conveyed out of the incubator, i.e. the time for which the overall portion having the length l [cm] is accommodated in the incubator.

From Formula (1) and $$v = n \cdot l \quad (2)$$

there obtains the formula $$L \geq (nt+1) \cdot l \quad (3)$$

With the first biochemical analysis apparatus in accordance with the present invention wherein the test film conveyance means continuously conveys at least the part of the long test film inside of the incubator at the speed v [cm/min.] and the length L of the incubator satisfies Formula (3), the incubation time does not obstruct quick processing when the sample application, incubation and measurement are carried out continuously and quickly.

Also, for an end point process wherein measurement is carried out when the incubation time t [min.] has elapsed, the measurement means may be provided at the position of $$M = v \cdot t + l \quad (4)$$

Substitution of Formula (2) into Formula (4) yields $$M = (nt+1) \cdot l \quad (5)$$

With the second biochemical analysis apparatus in accordance with the present invention, the test film conveyance means continuously conveys at least the part of the long test film inside of the incubator at the speed v [cm/min.], the length L of the incubator satisfies Formula (3), and the measurement means is provided at the position satisfying Formula (5). Therefore, the incubation time does not obstruct quick processing when the sample application, incubation and measurement are carried out continuously and quickly in an apparatus for measuring by the end point process.

With the third and fourth biochemical analysis apparatuses in accordance with the present invention wherein the incubator has the length adapted to accommodation of a plurality of sample-applied portions in the direction of conveyance of the long test film, a plurality of the sample-applied portions can be incubated simultaneously, and therefore incubation processing per unit time can be increased over an apparatus wherein a single sample-applied portion is incubated at one time. Also, in the case where the sample application is carried out sequentially for a plurality of portions of the long test film, the time elapsed after the start of the incubation differs among a plurality of the sample-applied portions. However, with the third biochemical analysis apparatus in accordance with the present invention wherein the measurement means is moveable along the part of the long test film inside of the incubator, and with the fourth biochemical analysis apparatus in accordance with the present invention wherein a plurality of the measurement means are provided along the part of the long test film inside of the incubator, a predetermined sample-applied portion can be measured when a predetermined time has elapsed after the start of the incubation.

With the third and fourth biochemical analysis apparatuses in accordance with the present invention wherein a plurality of the sample-applied portions are incubated simultaneously and the measurement means is moveable or a plurality of the measurement means are provided, sequential processing can be carried out quickly. Also, as the measurement means is moveable or a plurality of the measurement means are provided, the use efficiency of the long test film can be maximized regardless of the end point process wherein the optical density is measured after the incubation is carried out for a predetermined time and a rate process wherein the optical density is measured multiple times during the incubation and a change in the density is investigated.

With the fifth biochemical analysis apparatus in accordance with the present invention wherein at least the part of the long test film inside of the incubator is continuously moved reciprocally in the length direction of the long test film, a predetermined sample-applied portion can be moved to the position of the measurement means and measured when a predetermined time has elapsed after the start of the incubation. This operation can be carried out for each of a plurality of the sample-applied portions of the long test film to which the liquid sample has been applied sequentially. Also, with the fifth biochemical analysis apparatus in accordance with the present invention wherein the incubator has the length of $L \geq 2l \cdot (nt+1)$ and the measurement means is provided at the position of $l \cdot (nt+1) \leq M \leq L - l \cdot (nt+1)$, the sample-applied portion of the long test film does not come out of the incubator when the sample-applied portion is moved for the measurement, and the incubation can be carried out continuously.

In the fifth biochemical analysis apparatus in accordance with the present invention, the incubation time t [min.] is defined as the time for which the overall portion having the length l [cm] with a liquid sample applied thereon in a single step of sample application is accommodated in the incubator.

With the configuration of the fifth biochemical analysis apparatus in accordance with the present invention, sequential processing can be carried out quickly and the use efficiency of the long test film can be maximized in both the end point process and the rate process.

In the sixth and seventh biochemical analysis apparatuses in accordance with the present invention, the long test film is conveyed intermittently by a distance equal to the length l [cm] necessary for a singe sample application step at one time. FIG. 8 shows the temporal movement condition of the portion of the long test film, on which the liquid sample has been applied in a single step, in the incubator. With reference to FIG. 8, a period $\tau$ [min.] of the intermittent conveyance of the long test film is expressed as $$\tau = \tau 1 + \tau 2 \tag{6}$$

where $\tau 1$ [min.] denotes each stop time for which the long test film is stopped in the intermittent conveyance, and $\tau 2$ [min.] denotes each movement time between the start of the movement of the long test film 3 after the stop time $\tau 1$ [min.] and the stop at the next stop position after the movement by a distance equal to the length l [cm]. Therefore, the number n [number/min.] of repetitions of the sample application per minute is expressed as $$n = \frac{1}{\tau_1 + \tau_2} = \frac{1}{\tau} \tag{7}$$

In this case, the incubation time t.[min.] is defined as the time from when the overall portion having the length l [cm] on which a liquid sample has been applied in a single step of sample application is conveyed into the incubator to when the portion having the length l [cm] is at least partially conveyed out of the incubator, i.e. the time for which the overall portion having the length l [cm] is accommodated in the incubator.

In the case where the long test film is conveyed continuously so that the conveyance speed v [cm/min.] is expressed as $$v = \frac{l}{\tau} = n \cdot l \tag{8}$$

as indicated by the rightwardly-rising, parallel straight lines in FIG. 8, in order that the overall sample-applied portion having the length l [cm] is accommodated in the incubator for the incubation time t [min.], the length L" [cm] of the incubator should satisfy the condition $$L'' \geq v \cdot t + l = (nt+1) \cdot l \tag{9}$$

However, in the sixth and seventh biochemical analysis apparatuses in accordance with the present invention, the long test film is conveyed intermittently so that it stops for the time $\tau 1$ [min.] and moves for the time $\tau 2$ [min.]. Also, as shown in FIG. 8, an end point t0 of the stop time $\tau 1$ [min.] is generally selected as the end of the incubation time t [min.]. Therefore, the necessary length L (i.e. L') [cm] of the incubator should satisfy the condition $$L \geq [nt+1] \cdot l \tag{10}$$

where [nt+1] denotes the largest integer within the range not larger than nt+1.

With the sixth biochemical analysis apparatus in accordance with the present invention, the test film conveyance means intermittently conveys at least the part of the long test film inside of the incubator by a distance equal to the length l [cm] at one time, and the incubator is constituted so that the length L [cm] satisfies the condition of Formula (10). Therefore, the incubation time does not obstruct quick processing when the sample application, incubation and measurement are carried out continuously and quickly.

Also, in the end point process, the measurement means may be provided at the position for measuring the optical density when incubation time t [min.] has elapsed. Therefore, the distance M [cm] is expressed as $$M = [nt+1] \cdot l \qquad (11)$$

With the seventh biochemical analysis apparatus in accordance with the present invention, the test film conveyance means intermittently conveys at least the part of the long test film inside of the incubator by a distance equal to the length l [cm] at one time, the incubator is constituted so that the length L [cm] satisfies the condition of Formula (10), and the measurement means is provided at the position satisfying the condition of Formula (11). Therefore, the incubation time does not obstruct quick processing when the sample application, incubation and measurement are carried out continuously and quickly in the apparatus for measuring the optical density by the end point process.

With the eighth biochemical analysis apparatus in accordance with the present invention, the test film conveyance means intermittently conveys the part of the long test film inside of the incubator toward the outlet of the incubator by a distance equal to the length l [cm] necessary for a single step of sample application at one time. At the time the optical density is to be measured, the test film conveyance means reciprocally moves the part of the long test film inside of the incubator so that the sample-applied portion of the long test film the optical density of which is to be measured is moved to the position of the measurement means. Therefore, a predetermined sample-applied portion can be moved to the position of the measurement means and measured when a predetermined time has elapsed after the start of the incubation. This operation can be carried out for each of a plurality of the sample-applied portions of the long test film to which the liquid sample has been applied sequentially. Also, with the eighth biochemical analysis apparatus in accordance with the present invention wherein the incubator has the length of $L \geq 2l \cdot [nt+1]$ and the measurement means is provided at the position of $l \cdot [nt+1] \leq M \leq L - l \cdot [nt+1]$, the sample-applied portion of the long test film does not come out of the incubator when the sample-applied portion is moved for the measurement, and the incubation can be carried out continuously.

In the eighth biochemical analysis apparatus in accordance with the present invention, the incubation time t [min.] is defined as the time for which the overall portion having the length l [cm] with a liquid sample applied thereon in a single step of sample application is accommodated in the incubator.

With the configuration of the eighth biochemical analysis apparatus in accordance with the present invention, sequential processing can be carried out quickly and the use efficiency of the long test film can be maximized in both the end point process and the rate process.

BRIEF DESCRIPTION OF THE DRAWINGS

FIG. 8 is a graph showing the temporal movement condition of the portion of the long test film, on which the liquid sample has been applied in a single step, in the incubator, FIG. 12 is a sectional view taken along line X—X' of FIG. 2 and showing an embodiment of the fourth biochemical analysis apparatus in accordance with the present invention.

DESCRIPTION OF THE PREFERRED EMBODIMENTS

The present invention will hereinbelow be described in further detail with reference to the accompanying drawings.

Figure 1:
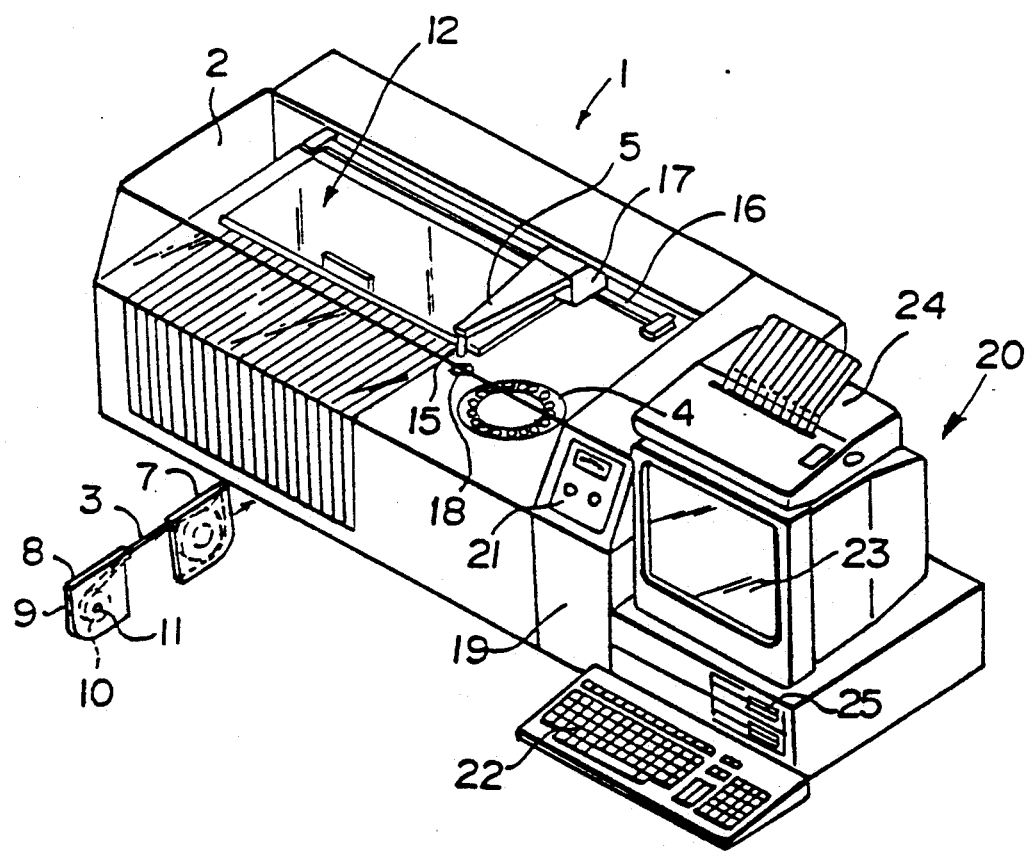
FIG. 1 is a perspective view showing an embodiment of the first biochemical analysis apparatus in accordance with the present invention.

With reference to FIG. 1 showing an embodiment of the first biochemical analysis apparatus in accordance with the present invention, a biochemical analysis apparatus 1 is provided with a transparent cover 2, and a liquid sample, a long tape-like test film 3 and the like are fed into and out of the apparatus 1 by opening the cover 2. The apparatus 1 is provided with a sample accommodating means 4 for accommodating a liquid sample such as blood serum or urine along a ring-like area, and the liquid sample is taken up from the sample accommodating means 4 and applied onto the long test film 3 by a sample application means 5 as will be described later.

The long test film 3 contains a reagent undergoing a color reaction with only a specific chemical constituent or a specific physical constituent that is to be analyzed in the liquid sample, and many kinds of the long test films 3, 3, . . . are prepared in accordance with the measurement items. An unused portion of the long test film 3 which has not yet been used for measurement is wound up in a film feed cassette 7, and the used portion of the long test film 3 which has already been used for measurement is wound up in a film wind-up cassette 8. The lot number, film number, measurement item, working life and other information on the long test film 3 are indicated by, for example, a bar code 9, on one face of the film wind-up cassette 8. At the center of a reel 10 in the film wind-up cassette 8, a hole 11 is provided for engagement with a rotation shaft of a motor for pulling the long test film 3 out of the film feed cassette 7 after the long test film 3 has been accommodated in the biochemical analysis apparatus 1 as will be described later. The long test film 3 is accommodated in the biochemical analysis apparatus 1 in the form wound up in the film feed cassette 7 and the film wind-up cassette 8. As shown in FIG. 1, the film feed cassette 7 and the film wind-up cassette 8 are formed independently of each other. A test film accommodating means 12 accommodates unused portions of a plurality of the long test films 3, 3, . . . in parallel so that various items of measurements can be carried out simultaneously by use of the apparatus 1. The sample application means 5 is provided with a sample applying nozzle 15 at the end, and is moved in the extending direction of a rail 16 by a movement means 17 placed on the rail 16 for taking up the liquid sample from the sample accommodating means 4, and applying the liquid sample onto the long test film 3 pulled out by a test film conveyance means from the test film accommodating means 12. The movement means 17 also moves the sample application means 5 vertically. The sample application means 5 is kept at its upper position at the time it is moved by the movement means 17 in the extending direction of the rail 16, and is moved down at the time of taking out and application of the liquid sample and at the time of washing as will be described later.

After applying the liquid sample onto the test film, the sample applying nozzle 15 is washed at a nozzle washing region 18 provided close to the test film accommodating means 12 and the sample accommodating means 4 therebetween, and is reused for sample application.

The test film on which the liquid sample has already been applied is incubated by an incubator as will be described later, and subjected to measurement by a measurement means.

Control of operations of the overall apparatus 1, processing of the measurement data and the like are carried out by a circuit region 19 and a computer 20 connected therewith. An operating and display region 21 on the front surface of the circuit region 19 is provided with a power source switch for the apparatus 1, an ammeter for monitoring the current consumption in the apparatus 1, and other members. The computer 20 is provided with a keyboard 22 for giving instructions to the apparatus 1, a CRT display device 23 for displaying the subsidiary information for instructions, measurement results and other items, a printer 24 for printing the measurement results, and a floppy disk drive unit 25 for accommodating a floppy disk for storage of commands for giving various instructions to the apparatus 1 and the information on the measurement results.

Figure 2:
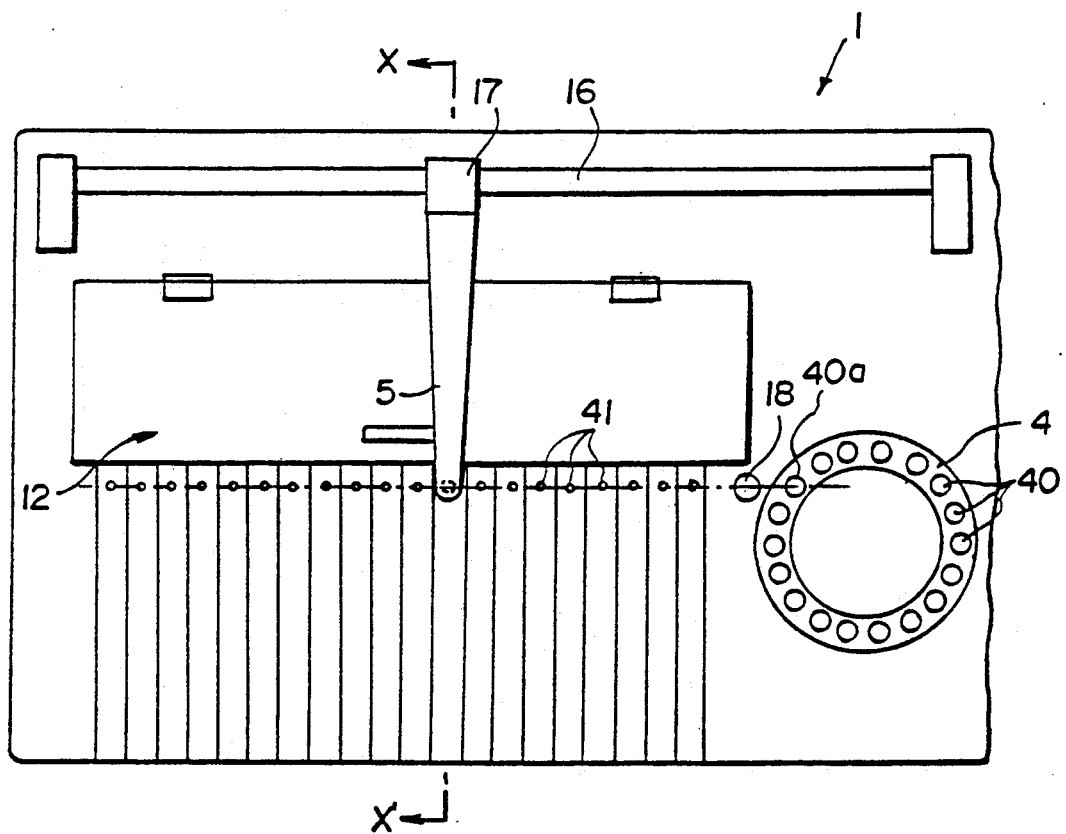
FIG. 2 is a plan view showing the major part of the embodiment shown in FIG. 1.

With reference to FIG. 2 showing the major part of the apparatus 1, the test film accommodating means 12 is constituted so that sample applying positions 41, 41, . . . for all of the test films pulled out of the test film accommodating means 12 stand in a straight line indicated by the chain line. Also, the nozzle washing region 18 and a liquid sample take-out position 40a in the sample accommodating means 4 are disposed on said straight line. The arrangement of the aforesaid positions and the nozzle washing region 18 on the straight line simplifies the configuration of the movement means as will be described later, which in turn contributes to a decrease in operation failures and cost of the apparatus 1.

The sample accommodating means 4 accommodates a plurality of sample cups containing liquid samples in accommodating regions 40, 40, . . . disposed in the ring-like area. A sensor for detecting whether the sample cup has been accommodated is provided at each of the accommodating regions 40, 40, . . . When the accommodation of the sample cup is detected by the sensor, information indicating the accommodation of the sample cup and the accommodating position is transmitted to the computer 20 via the circuit region 19 shown in FIG. 1, and a warning is issued to the operator by sound, light or the like for requesting entry of information on the liquid sample contained in said sample cup and entry of instructions (for example, ID information for identifying the liquid sample and the measurement item for the liquid sample) from the keyboard 22. Alternatively, no warning may be issued, and the information and instructions which are to be entered are displayed on the CRT display. Erroneous entry and entry failure can be prevented in the case where the accommodating position is detected automatically and entry of the information and instructions on the liquid sample contained in the sample cup is requested at the time the sample cup is accommodated in each of the accommodating regions 40, 40, . . . In the case where take-out of the sample cup from the accommodating region 40 is detected by the sensor before the liquid sample is taken by the sample application means 5 out of the accommodated sample cup for the purpose of measurement, a warning is issued to the operator.

The accommodating regions 40, 40, . . . are automatically rotated by a rotation means (not shown) along the circular path until the liquid sample which is accommodated in one of the accommodating regions 40, 40, . . . and which is to be used for the next measurement arrives at the take-out position 40a. In order to prevent the liquid samples accommodated in the accommodating regions 40, 40, . . . from evaporating and deteriorating, a cover (not shown) is provided on the accommodating regions 40, 40, . . . outside of the take-out position 40a.

The sample application means 5 is moved by the movement means 17 in the extending direction of the rail 16, takes up the liquid sample from the take-out position 40a, and applies it to the sample applying position 41 on the test film.

Figure 3:
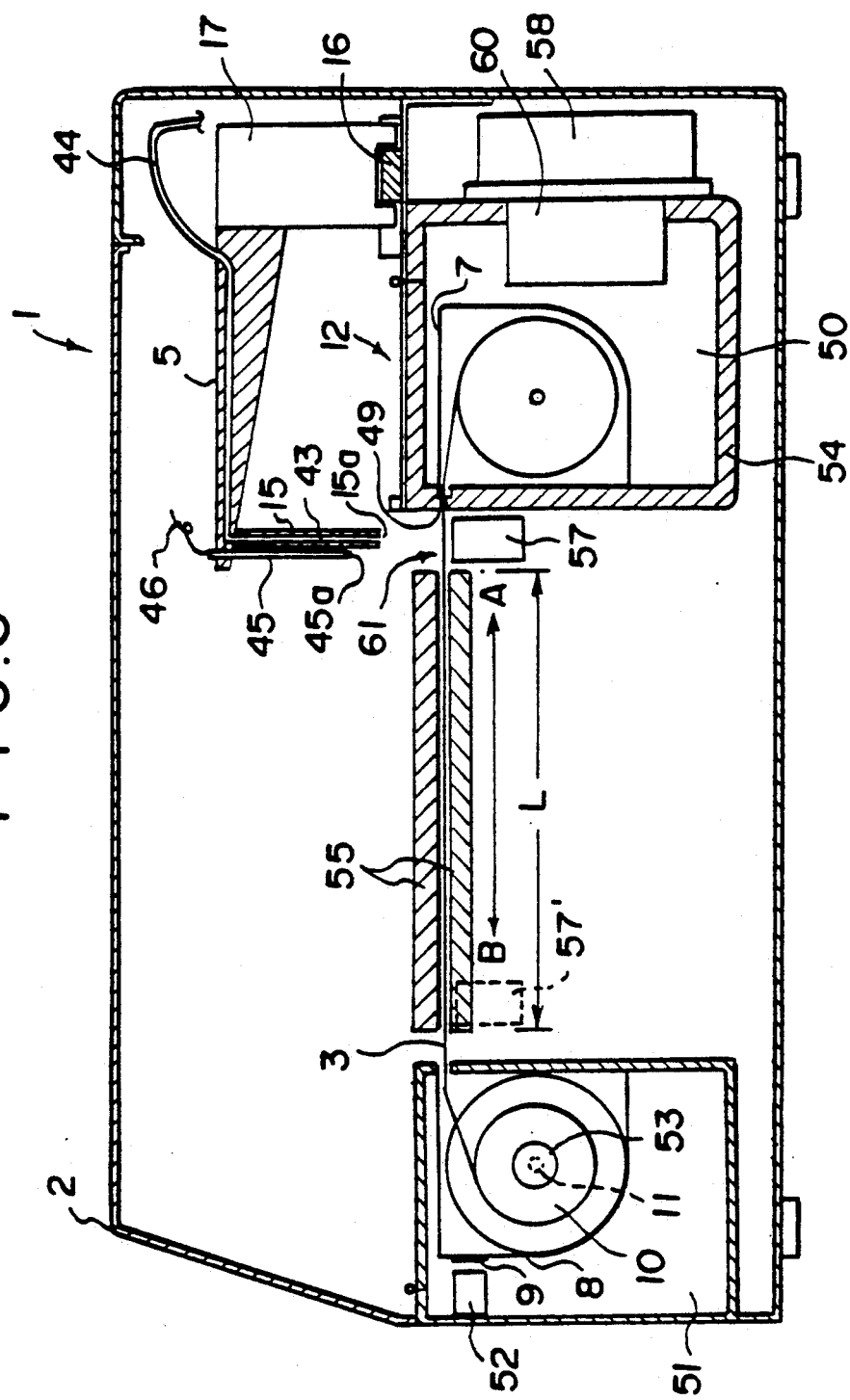
FIG. 3 is a sectional view taken along line X—X' of FIG. 2.

FIG. 3 is a sectional view taken along line X—X' of FIG. 2. In FIG. 3, similar elements are numbered with the same reference numerals with respect to FIGS. 1 and 2. With reference to FIG. 3, the long test film 3 is accommodated in the film feed cassette 7 and the film wind-up cassette 8 and is accommodated in this form in the apparatus 1. The film feed cassette 7 is accommodated in a refrigerator 50 which constitutes the test film accommodating means 12, and the film wind-up cassette 8 is accommodated in a wind-up chamber 51.

With the configuration wherein the unused portion of the long test film 3 is accommodated in the film feed cassette 7, the unused long test film 3 can be accommodated in the test film accommodating means 12 without the hands of the operator contacting the unused long test film 3.

As mentioned above, by way of example, the bar code 9 indicating the lot number, film number, measurement item, working life and other information on the long test film 3 is provided on one face of the film wind-up cassette 8. The information indicated by the bar code 9 is read by a bar code reading means 52 provided at a position in the wind-up chamber 51 corresponding to the position at which the bar code 9 is located when the film wind-up cassette 8 is accommodated in the wind-up chamber 51. The information thus read is stored on, for example, the floppy disk in the floppy disk drive unit 25 shown in FIG. 1, and is used for control of the measurement item and control of the length of the unused film portion remaining in the film feed cassette 7, and elimination of measurement errors caused by fluctuations among production lots of the long test films 3, 3, . . . Also, in the case where the long test film 3 is taken out of the apparatus 1 after being used partially, the film number, the length of the remaining unused film portion and other information on the long test film 3 are stored on the floppy disk unless a deletion command is entered from the keyboard 22 shown in FIG. 1 or until the information is deleted automatically at the time the long test film 3 runs out of the working life. When the long test film 3 is again accommodated in the test film accommodating means 12 for reuse, the film number of the long test film 3 is compared with the information stored on the floppy disk, and the length of the remaining unused portion of the long test film 3 and other items are controlled again.

The aforesaid bar code 9 may be provided on the film feed cassette 7, and the bar code reading means 52 may be provided inside of the refrigerator 50. Also, the means for transmitting the lot number, the working life and other information on the long test film 3 to the apparatus 1 is not limited to the bar code 9 and the bar code reading means 52, and any other means may be employed for this purpose insofar as the information can be recorded on the film feed cassette 7 or on the film wind-up cassette 8 and can be read at the time the long test film 3 is accommodated in the apparatus 1.

The refrigerator 50 is enclosed by a refrigerator wall 54 composed of a heat insulating material. A cooling and dehumidifying device 58 for keeping the inside of the refrigerator 50 at a predetermined low temperature and low humidity is provided on one surface of the refrigerator wall 54, and air inside of the refrigerator 50 is circulated by a fan 60.

When the film wind-up cassette 8 is accommodated in the wind-up chamber 51, a rotation shaft of a test film wind-up motor 53 constituting the test film conveyance means for the long test film 3 provided in the wind-up chamber 51 engages with a hole 11 formed at the center of a reel 10 of the film wind-up cassette 8. As the motor 53 is rotated, the long test film 3 is continuously pulled out of the film feed cassette 7 through a film outlet 49 of the refrigerator 50, and is wound up in the film wind-up cassette 8. The speed v [cm/min.] of said pull-out is expressed by $$v = n \cdot l$$

where l [cm] denotes the length of a portion of the long test film 3 necessary for a single step of sample application, and n [number/min.] denotes the number of repetitions of the sample application per minute.

With the configuration wherein the used portion of the long test film 3 is accommodated in the film wind-up cassette 8, the used long test film 3 on which the liquid sample has already been applied can be taken out of the apparatus 1 and discarded or processed for other purposes without the hands of the operator contacting the used long test film 3. For discarding the used long test film 3, instead of winding up the used film around the film wind-up cassette 8, the film wind-up cassette 8 may be omitted, a box for receiving the film and capable of being fitted to and removed from the apparatus 1 may be provided at the position of the wind-up chamber 51, a cutter for cutting the used film may be provided near the inlet of the region of the wind-up chamber 51, and the used film may be cut and accommodated in the box. With this configuration, the used film contained in the box can be taken out of the apparatus 1 together with the box and discarded or processed for other purposes without the hands of the operator contacting the used film. In this case, conveyance of the test film may be carried out by the provision of conveying rollers for grasping and conveying the test film.

An elongated pipe 43 continuing into a leading edge 15a of the sample applying nozzle 15 is provided in the sample application means 5. The pipe 43 is communicated with a flexible pipe 44 so that the liquid sample is fed through the pipes 43 and 44 into the sample application means 5 and applied onto the long test film 3. At the time the sample applying nozzle 15 is to be washed, the leading edge 15a of the sample applying nozzle 15 is immersed in a small vessel containing distilled water and provided at the nozzle washing region 18, and washing liquid is delivered from a tank (not shown) through the pipes 42 and 44.

A liquid level detector 45 is provided in parallel with the sample applying nozzle 15 in the vicinity thereof. The liquid level detector 45 is provided so that its leading edge 45a is slightly (for example, by approximately 2.5 mm) higher than the leading edge 15a of the sample applying nozzle 15. When the sample application means 5 is moved down by the movement means 17 for taking up the liquid sample accommodated in the sample accommodating means 4, the leading edge 15a of the sample applying nozzle 15 enters the liquid sample, and the leading edge 45a of the liquid level detector 45 contacts the liquid sample. At this time, a signal indicating that the leading edge 45a of the liquid level detector 45 has contacted the liquid sample is produced by the liquid level detector 45, and transmitted to the circuit region 19 shown in FIG. 1 through a signal line 46. Based on the signal, the downward movement of the sample application means 5 is stopped. In this manner, the leading edge 15a of the sample applying nozzle 15 can be entered into the liquid sample up to a predetermined depth from the surface of the liquid sample regardless of the amount of the liquid sample.

The exposed portion of the long test film 3 between the film feed cassette 7 and the film wind-up cassette 8 passes through an incubator 55 having the inside maintained at a predetermined temperature (for example, 37°). A measurement means 57 for measuring the optical density produced by a color reaction of the long test film 3 with the liquid sample is disposed on the lower side the incubator 55. The measurement means 57 is reciprocally moveable by a movement means (not shown) in the directions as indicated by the arrows A and B between a position (i.e. the position of the measurement means 57 indicated by the solid line) for measurement of the optical density of the long test film 3 at a sample applying position 61 at which the liquid sample is applied by the sample application means 5 and a position (i.e. a position 57' indicated by the broken line) at the tailing edge of the incubator 55 on the side of the wind-up chamber 51. In this manner, the measurement means 57 measures the background, i.e. the optical density of the long test film 3 without the liquid sample applied thereon, at the sample applying position 61, and the optical density at a plurality of the sample-applied portions of the long test film 3 inside of the incubator 55.

The length L [cm] of the incubator 55 in the direction of conveyance of the long test film 3 is defined as described below. Specifically, the incubator 55 has the length L [cm] expressed as $$L \geq v \cdot t + l \qquad (12)$$

where l [cm] denotes the length of a portion of the long test film 3 necessary for a single step of sample application, t [min.] denotes the time for which the sample-applied portion of the long test film 3 is to be maintained at a predetermined temperature inside of the incubator 55, n [number/min.] denotes the number of repetitions of the sample application per unit time, and v [cm/min.] denotes the wind-up speed at which the long test film 3 is continuously wound up by the wind-up motor 53. In this embodiment, the wind-up speed is equal to the speed at which the long test film 3 is pulled out of the film feed cassette 7, and the speed of conveyance of the pulled-out long test film 3 inside of the incubator 55. As mentioned above, the formula $$V = n \cdot l \qquad (13)$$

applies. Substitution of Formula (13) into Formula (12) yields $$L \geq (nt + 1) \cdot l \qquad (14)$$

In the case where the incubator 55 has the length expressed by L, the processing capacity of the apparatus 1 does not decrease even though a long time t [min.] is taken for the incubation.

In order to define the length L of the incubator 55, it is only necessary that the conveyance speed of the part of the long test film 3 be equal to v [cm/min.]. For example, the long test film 3 ma be intermittently pulled out of the film feed cassette 7, and a buffer for shifting the conveyance of the long test film 3 from the intermittent operation to the continuous operation may be provided between the refrigerator 50 and the sample applying position 61.

As mentioned above, the biochemical analysis apparatus 1 is constituted to simultaneously accommodate a plurality of the long test films 3, 3, . . . The incubation time t [min.] often differs among the long test films 3, 3, . . . for use in analysis of different chemical ingredients or the like. In this case, the length of the incubator 55 should preferably be adjusted to be equal to the length corresponding to the longest incubation time, so that a long test film 3 requiring a long incubation time may be accommodated at any position in the test film accommodating means 12. Also, in the case of a single-function type apparatus capable of accommodating only a single long test film 3, the length L [cm] of the incubator 55 is adjusted in accordance with a long test film 3 requiring the longest incubation time t [min.] among a plurality of the long test films 3, 3, . . . which are expected to be used in the apparatus.

Figure 4:
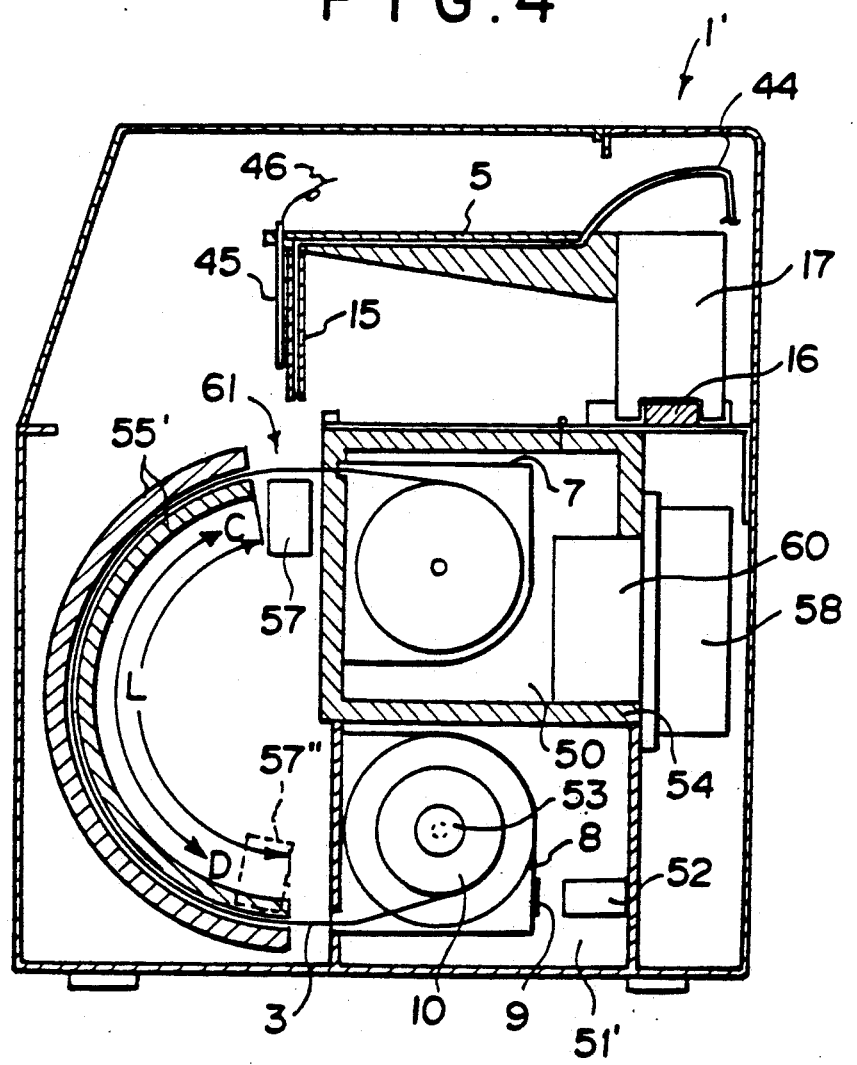
FIG. 4 is a sectional view showing another embodiment of the first biochemical analysis apparatus in accordance with the present invention.

FIG. 4 shows another embodiment of the first biochemical analysis apparatus in accordance with the present invention. In FIG. 4, similar elements are numbered with the same reference numerals with respect to FIG. 3.

With reference to FIG. 4, an incubator 55' of a biochemical analysis apparatus 1' is shaped in a circular arc-like form, and the measurement means 57 is reciprocally moveable by a movement means (not shown) in the directions as indicated by the arrows C and D along the circular arc between a position (i.e. the position of the measurement means 57 indicated by the solid line) for measurement of the optical density of the long test film 3 at the sample applying position 61 and a position (i.e. a position 57" indicated by the broken line) at the tailing edge of the incubator 55' on the side of a wind-up chamber 51'. In this manner, the measurement means 57 measures the background, i.e. the optical density of the long test film 3 without the liquid sample applied thereon, at the sample applying position 61, and the optical density at a plurality of the sample-applied portions of the long test film 3 inside of the incubator 55'.

The circular arc-like configuration of the incubator 55' is advantageous for making the apparatus 1' compact.

The conveyance speed v [cm/min.] of the part of the long test film 3 inside of the incubator 55' and the length L [cm] of the incubator 55' are defined in the same manner as in the embodiment shown in FIG. 3.

Figure 5:
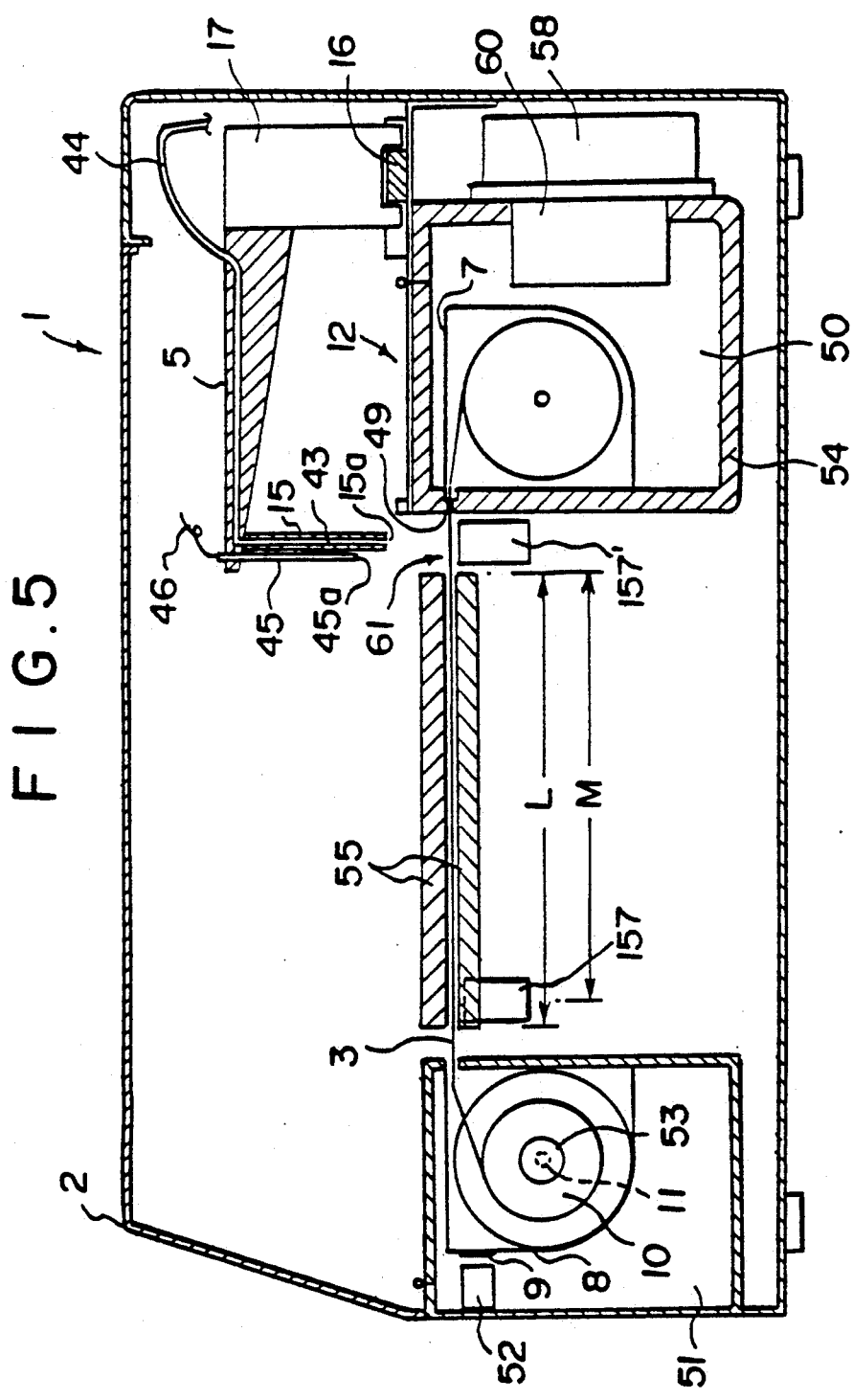
FIG. 5 is a sectional view taken along line X—X' of FIG. 2 and showing an embodiment of the second biochemical analysis apparatus in accordance with the present invention.

An embodiment of the second biochemical analysis apparatus in accordance with the present invention will hereinbelow be described with reference to FIGS. 5 and 6. In FIG. 5, similar elements are numbered with the same reference numerals with respect to FIG. 3.

With reference to FIG. 5, the length L [cm] of the incubator 55 in the direction of conveyance of the long test film 3 is defined in the same manner as in the embodiment shown in FIG. 3. Also, a distance M [cm] between the inlet of the incubator 55 for the long test film 3 and a measurement means 157 as measured from the inlet toward the outlet of the incubator 55 is defined as described below. Measurement by an end point process can be carried out by providing the measurement means 157 at a position of $$M = v \cdot t + l \qquad (15)$$

where l [cm] denotes the length of a portion of the long test film 3 necessary for a single step of sample application, t [min.] denotes the time for which the sample-applied portion of the long test film 3 is to be maintained at a predetermined temperature inside of the incubator 55, and v [cm/min.] denotes the wind-up speed. Substitution of Formula (7) into Formula (9) yields $$M = (nt + 1) \cdot l \qquad (16)$$

In the case where the incubator 55 has the length expressed by L, the processing capacity of the apparatus 1 does not decrease even though a long time t [min.] is taken for the incubation. Also, as the measurement means 157 is provided at the position indicated by M in Formula (16), measurement using the end point process can be carried out continuously by measuring the optical density of the sample-applied portion of the long test film 3 at the time the sample-applied portion passes over the measurement means 157.

In order to define the length L of the incubator 55 and the position of the measurement means 157, it is only necessary that the conveyance speed of the part of the long test film 3 be equal to v [cm/min.]. For example, the long test film 3 may be intermittently pulled out of the film feed cassette 7, and a buffer for shifting the conveyance of the long test film 3 from the intermittent operation to the continuous operation may be provided between the refrigerator 50 and the sample applying position 61.

Also, in the embodiment shown in FIG. 5, a measurement means 157' may be provided for measuring the optical density of the long test film 3 at the sample applying position 61 at which the liquid sample is applied by the sample application means 5. The background, i.e. the optical density of the long test film 3 without the liquid sample applied thereon, may be measured by the measurement means 157', and the value measured by the measurement means 157 after the sample application and incubation are carried out may be corrected based on the measured value. In this manner, the measurement accuracy can be improved.

As mentioned above, in this embodiment, the biochemical analysis apparatus 1 is constituted to simultaneously accommodate a plurality of the long test films 3, 3, . . . The incubation time t [min.] often differs among the long test films 3, 3, . . . for use in analysis of different chemical ingredients or the like. In this case, the length of the incubator 55 should preferably be adjusted to be equal to the length corresponding to the longest incubation time, so that a long test film 3 requiring a long incubation time may be accommodated at any position in the test film accommodating means 12. In this case, the measurement means 157 is manually or automatically moved to the position corresponding to the incubation time for the accommodated long test film 3. Also, in the case of a single-function type apparatus capable of accommodating only a single long test film 3, the length L [cm] of the incubator 55 is adjusted in accordance with a long test film 3 requiring the longest incubation time t [min.] among a plurality of the long test films 3, 3, . . . which are expected to be used in the apparatus, and the measurement means 157 is manually or automatically moved to the position corresponding to the incubation time for the accommodated long test film 3.

Figure 6:
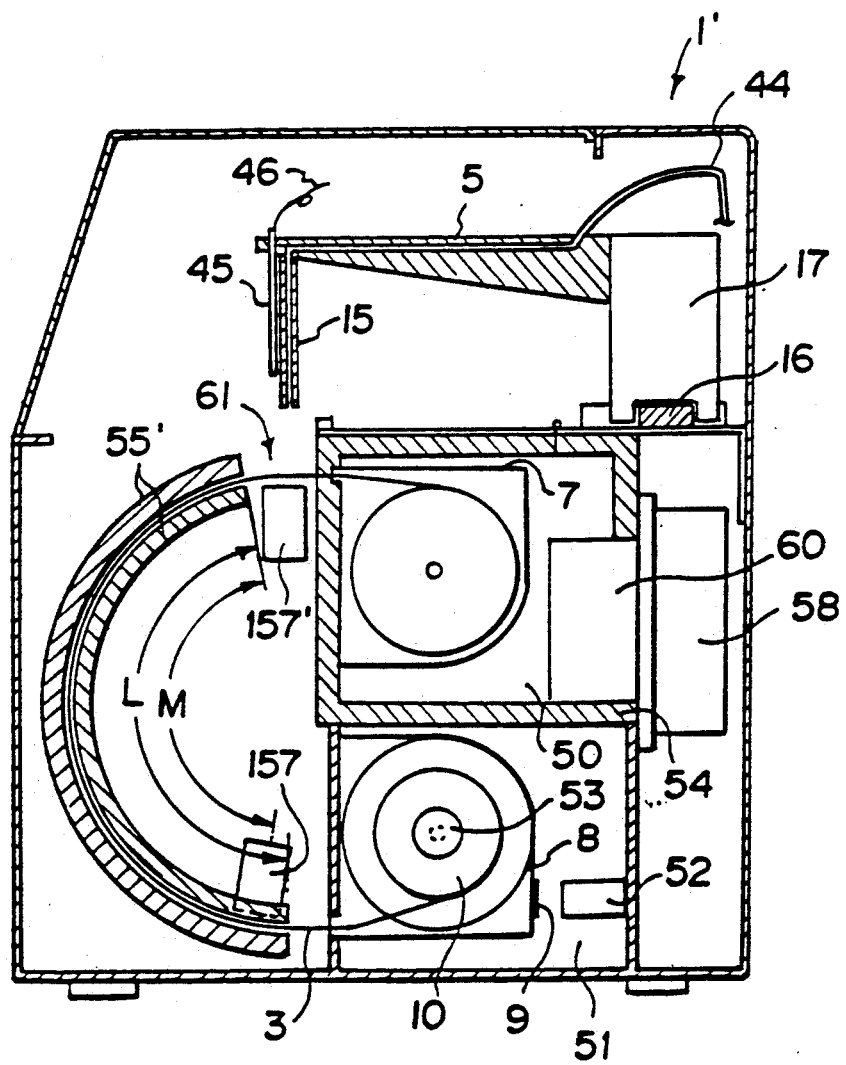
FIG. 6 is a sectional view showing another embodiment of the second biochemical analysis apparatus in accordance with the present invention.

FIG. 6 shows another embodiment of the second biochemical analysis apparatus in accordance with the present invention. In FIG. 6, similar elements are numbered with the same reference numerals with respect to FIG. 5.

With reference to FIG. 6, the incubator 55' of the biochemical analysis apparatus 1' is shaped in a circular arc-like form.

The circular arc-like configuration of the incubator 55' is advantageous for making the apparatus 1' compact.

The conveyance speed v [cm/min.] of the part of the long test film 3 inside of the incubator 55', the length L [cm] of the incubator 55', and the position M [cm] of the measurement means 157 are defined in the same manner as in the embodiment shown in FIG. 5.

Figure 7:
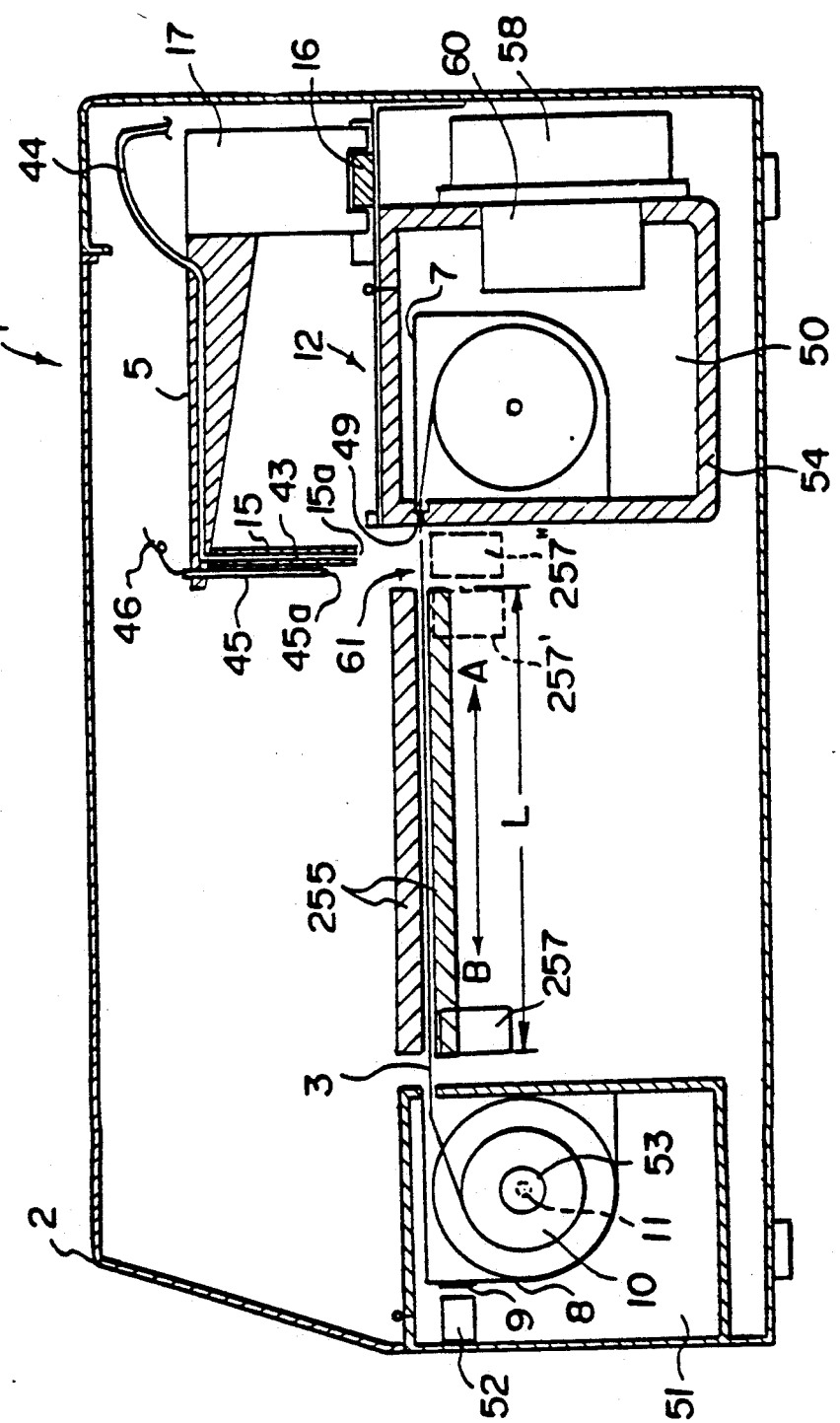
FIG. 7 is a sectional view taken along line X—X' of FIG. 2 and showing an embodiment of the third biochemical analysis apparatus in accordance with the present invention.

An embodiment of the third biochemical analysis apparatus in accordance with the present invention will hereinbelow be described with reference to FIGS. 7 to 11. In FIG. 7, similar elements are numbered with the same reference numerals with respect to FIG. 3.

With reference to FIG. 7, the long test film 3 is continuously or intermittently pulled out of the film feed cassette 7, and wound in the film wind-up cassette 8. A measurement means 257 is reciprocally moveable by a movement means (not shown) in the directions as indicated by the arrows A and B between a position (i.e. the position of the measurement means 257 indicated by the solid line) at an edge of an incubator 255 on the side of the wind-up chamber 51 and a position (i.e. a position 257' indicated by the broken line) at the other edge of the incubator 255. In this manner, the measurement means 257 measures the optical density at a plurality of the sample-applied portions of the long test film 3 inside of the incubator 255.

Since the measurement means 257 measures by moving as mentioned above, it cannot simultaneously measure a plurality of the sample-applied portions. However, in the end point process, measurement may be carried out sequentially with the same period as the period of sequential sample application, and therefore a plurality of the sample-applied portions need not be simultaneously measured. On the other hand, in the rate process, even though a plurality of the sample-applied portions cannot be measured simultaneously, the change caused by a color formation progresses temporally continuously, and therefore the measured values can be corrected as the time at which the measurement is carried out deviates slightly.

The measurement means 257' may be provided moveably also to a position 257" indicated by the broken line for measuring the background, i.e. the optical density of the long test film 3 at the sample applying position 61 without the liquid sample applied thereon. The value measured by the measurement means 257 after the sample application and incubation are carried out may be corrected based on the measured value. In this manner, the measurement accuracy can be improved.

The length L [cm] of the incubator 255 in the direction of conveyance of the long test film 3 will hereinbelow be described with reference to FIG. 8.

FIG. 8 shows the relationship between the necessary incubation time t [min.] and the necessary length L (i.e. L' or L") [cm] of the incubator 255.

With reference to FIG. 8, the hatched region surrounded by rightwardly rising, parallel straight lines indicates the temporal movement condition of a portion having a length l [cm], on which a liquid sample has been applied in a single step of sample application, inside of the incubator 255 in the case where the long test film 3 is continuously conveyed at a predetermined speed.

In the case where the long test film 3 is conveyed continuously at a predetermined speed v [cm/min.], the necessary length L" (continuous feed) [cm] of the incubator 255 is expressed as $$L'' = v \cdot t + l \tag{17}$$

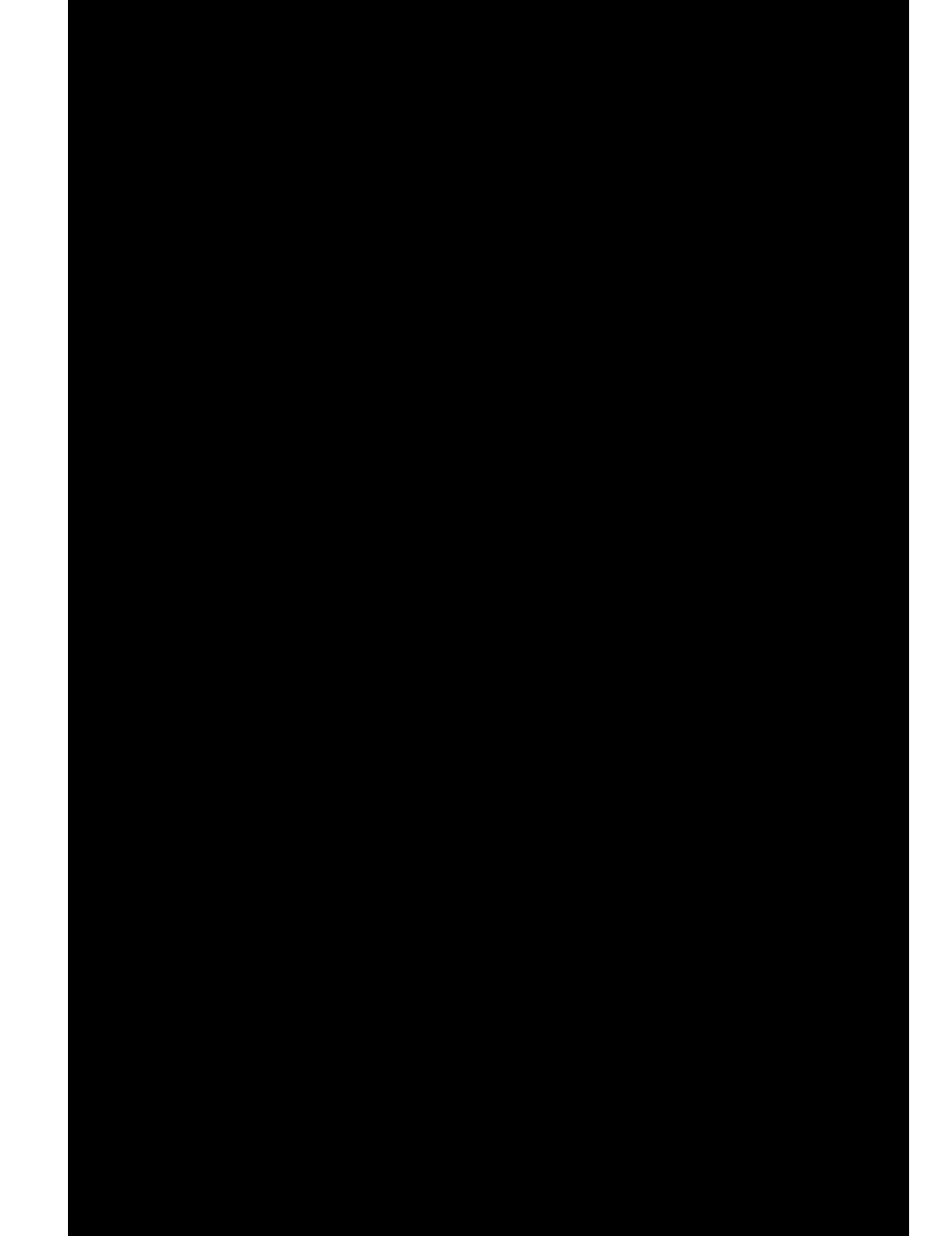

after the incubation has been carried out for the predetermined time is employed, instead of the rate process for measuring the optical density at a plurality of the sample-applied portions during the incubation. However, in this case, portions 63, 63, ... of the long test film 3 remain unused, and the use efficiency of the long test film 3 decreases. On the other hand, in the case where the rate process is employed, it is necessary for the measurement means 257 to move also when the apparatus is constituted to always convey the long test film 3 with the predetermined period $\tau$ [min.] as shown in FIG. 9A.

Figure 9A:
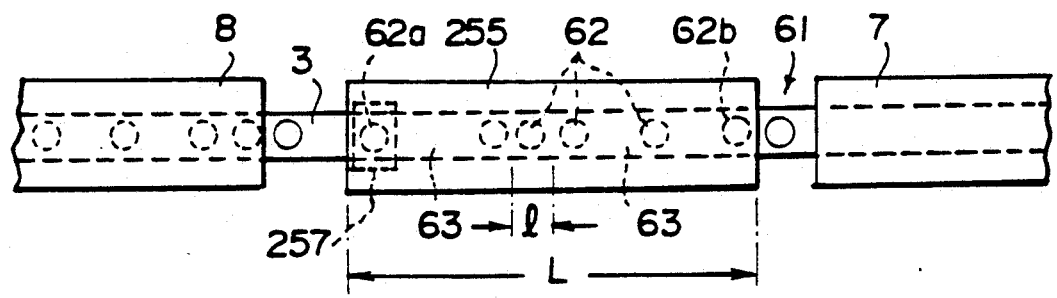
FIGS. 9A and 9B are explanatory views showing the condition of sample application onto a long test film in the embodiment shown in FIG. 7.
Figure 9B:
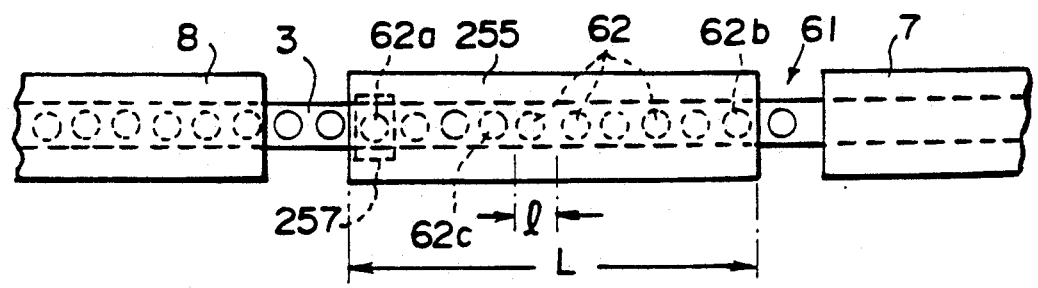

FIG. 9B shows an example wherein the apparatus is constituted to make the long test film 3 wait without conveying it in the case where the measurement corresponding to the long test film 3 is not carried out. In FIG. 9B, similar elements are numbered with the same reference numerals with respect to FIG. 9A. In this case, the long test film 3 may often wait for some time without being conveyed. Therefore, the predetermined incubation time may have already elapsed with the sample-applied portion being located at, for example, a position 62c also in the case where the end point process is employed. In this case, the measurement means 257 is moved to the position 62c, and measures the optical density of the sample-applied portion at the position 62c.

With this embodiment wherein the movement means 257 is moveable, the measurement using the rate process can be carried out, and the use efficiency of the long test film 3 can be maximized by the utilization of the control method corresponding to FIG. 9B in both the end point process and the rate process.

Figure 10:
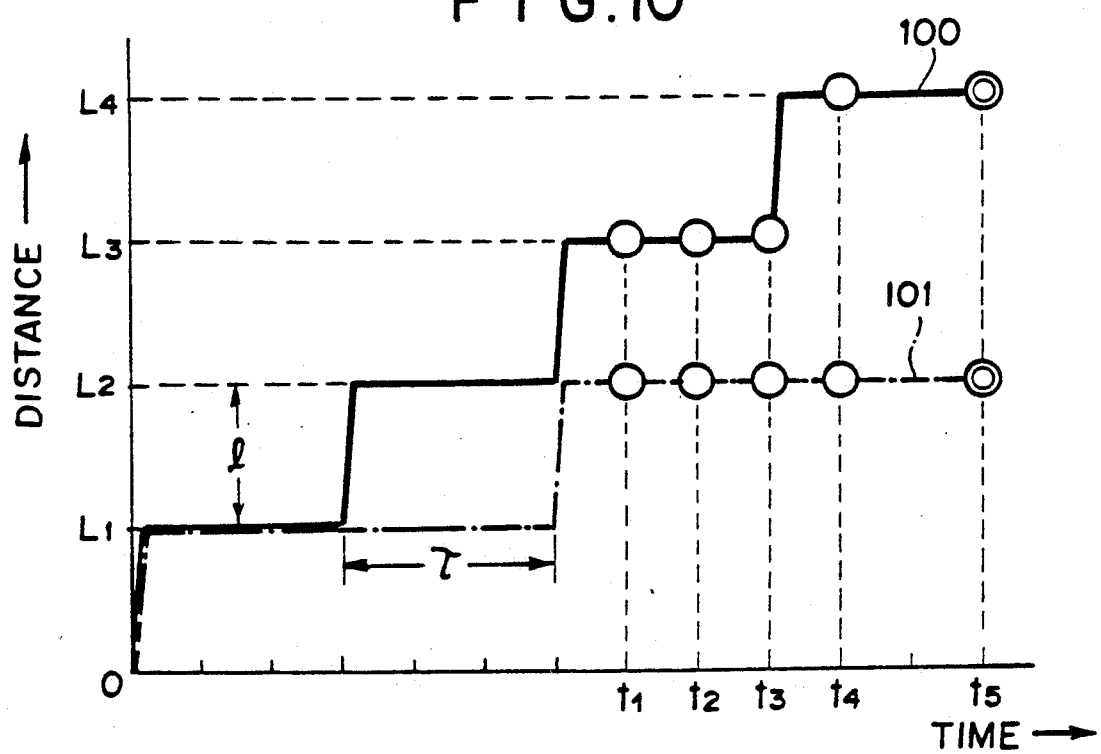
FIG. 10 is a graph showing an example of the relationship between the movement of a sample-applied portion and the movement of a measurement means.

FIG. 10 shows examples of the relationships between the movement of the sample-applied portion 62 in the incubator 255 and the movement of the measurement means 257 shown in FIGS. 9A and 9B. The horizontal axis denotes the time as counted from when the sample-applied portion 62 has been accommodated in the incubator 255, and the vertical axis denotes the distance inside of the incubator 255 as measured from the edge of the incubator 255 on the side of the sample applying position 61 toward the opposite edge of the incubator 255. The single circle indicates the time and the distance in the case where the measurement is carried out by use of the rate process, and the double circle indicates the time and the distance in the case where the measurement is carried out by use of the end point process. In FIG. 10, for simplicity of explanation, it is assumed that only four sample-applied portions can be accommodated in the incubator 255, and the movement of only a single sample-applied portion is shown.

A graph 100 is for the case where the long test film 3 is conveyed by use of the control method illustrated in FIG. 9A. In the case where the end point process is employed, a distance L4 is fixed and the measurement means 257 measures at the time t5. In the case of the rate process, the measurement means 257 is located at the distance L3 to measure the optical density of a sample-applied portion at the time t1, the time t2 and the time t3. When the sample-applied portion is moved to the distance L4, the measurement means 257 is moved to the distance L4 and measures at the time t4. In this manner, the measurement means 257 is controlled to move in accordance with the movement of the sample-applied portion. In the case where a plurality of the sample-applied portions 62, 62, ... are simultaneously present inside of the incubator 255 and the measurement is carried out by the rate process, the measurement means 257 is moved to carry out the measurement for the respective sample-applied portions 62, 62, ... in the manner as mentioned above. Also, as mentioned above, the measured value can be corrected when a plurality of the sample-applied portions cannot be measured simultaneously.

A graph 101 is for the case where the long test film 3 is conveyed by use of the control method illustrated in FIG. 9B. In this case, as indicated by the graph 101, the sample-applied portion 62 may be present at the distance L2 also at the time t5 for the measurement by the end point process. In this case, the measurement means 257 is moved to the distance L2 for carrying out the measurement. In the example of the graph 101, when the rate process is employed, the measurement means 257 is located at the distance L2, and measures at the time t1, the time t2, the time t3 and the time t4. When the control method corresponding to FIG. 9B is employed in this manner, the measurement is carried out by moving the measurement means 257 in both the rate process and the end point process. In the case where a plurality of the sample-applied portions 62, 62, ... are simultaneously present inside of the incubator 255, the measurement means 257 is moved to carry out the measurement for the respective sample-applied portions 62, 62, ... in the manner as mentioned above.

Figure 11:
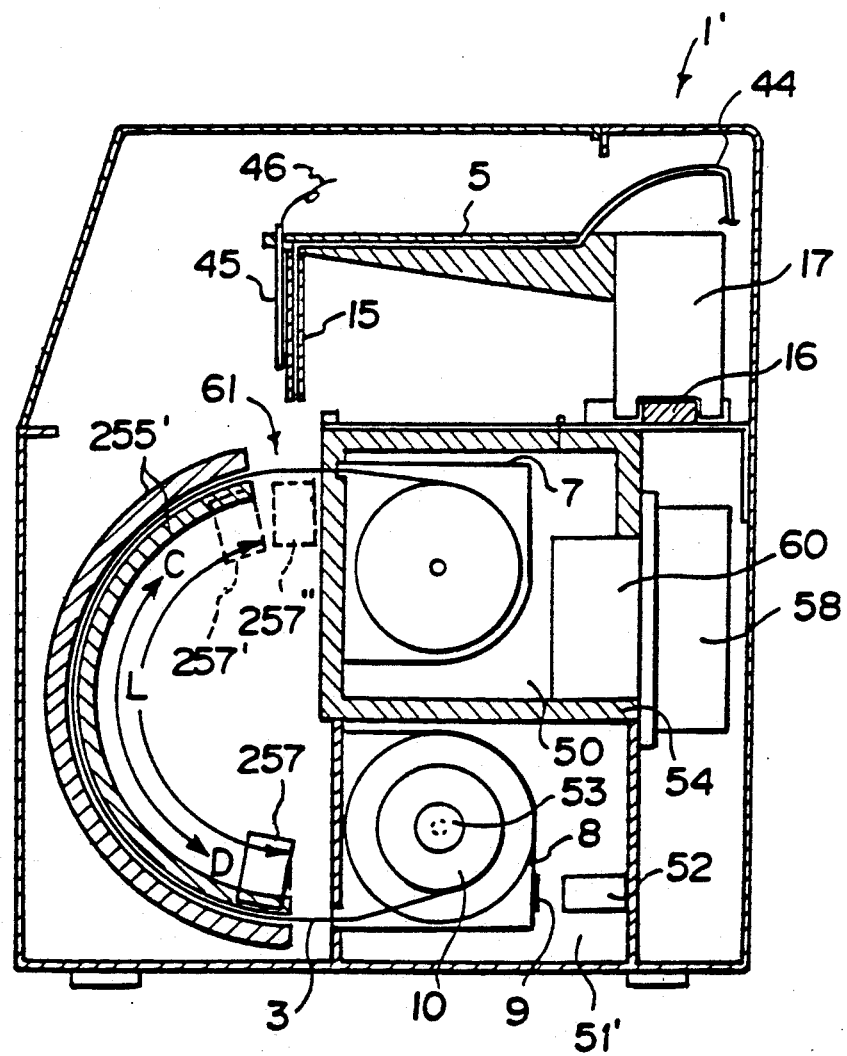
FIG. 11 is a sectional view showing another embodiment of the third biochemical analysis apparatus in accordance with the present invention.

FIG. 11 is a sectional view showing another embodiment of the third biochemical analysis apparatus in accordance with the present invention. In FIG. 11, similar elements are numbered with the same reference numerals with respect to FIG. 7.

With reference to FIG. 11, an incubator 255' of a biochemical analysis apparatus 1' is shaped in a circular arc form, and the measurement means 257 is reciprocally moveable by a movement means (not shown) in the directions as indicated by the arrows C and D between a position (i.e. the position of the measurement means 257 indicated by the solid line) at an edge of an incubator 255' on the side of a wind-up chamber 51' and a position (i.e. a position 257' indicated by the broken line) at the other edge of the incubator 255'. In this manner, the measurement means 257 measures the optical density at a plurality of the sample-applied portions of the long test film 3 inside of the incubator 255'. The measurement means 257' may be provided moveably also to a position 257" indicated by the broken line for measuring the background, i.e. the optical density of the long test film 3 at the sample applying position 61 without the liquid sample applied thereon.

The circular arc-like configuration of the incubator 255' is advantageous for making the apparatus 1' compact and for simplifying the mechanism for the movement of the movement means 257.

The length L [cm] of the incubator 255' is defined in the same manner as in the embodiment shown in FIG. 7.

An embodiment of the fourth biochemical analysis apparatus in accordance with the present invention will hereinbelow be described with reference to FIGS. 12 to 14. In FIG. 12, similar elements are numbered with the same reference numerals with respect to FIG. 3.

With reference to FIG. 12, the long test film 3 is continuously or intermittently pulled out of the film feed cassette 7, and wound in the film wind-up cassette 8.

A plurality of measurement means 357, 357, ... are provided at intervals of the length l [cm] of the long test film 3 necessary for a single step of sample application to correspond to a plurality of sample-applied portions of the long test film 3 inside of the incubator 255, thereby to measure the optical density of the sample-applied portions.

In the case where the measurement means 357, 357, . . . are provided in this manner, the optical density cannot be measured at the middle between two adjacent measurement means 357, 357. However, the change caused by a color formation progresses temporally continuously, and the measured values can be corrected as the time at which the measurement is carried out deviates slightly. Therefore, no problem arises when the optical density cannot be measured at the middle between two adjacent measurement means 357, 357.

A measurement means 357' may also be provided to measure the background, i.e. the optical density of the long test film 3 without the liquid sample applied thereon, at the sample applying position 61. Values measured by the measurement means 357, 357, . . . after the sample application and incubation have been carried out may be corrected based on the measured background density. In this manner, the measurement accuracy can be improved.

The length l [cm] of the incubator 255 in the direction of conveyance of the long test film 3 is defined in accordance with the continuous feed and the intermittent feed in the same manner as in the embodiment shown in FIG. 7.

Figure 13A:
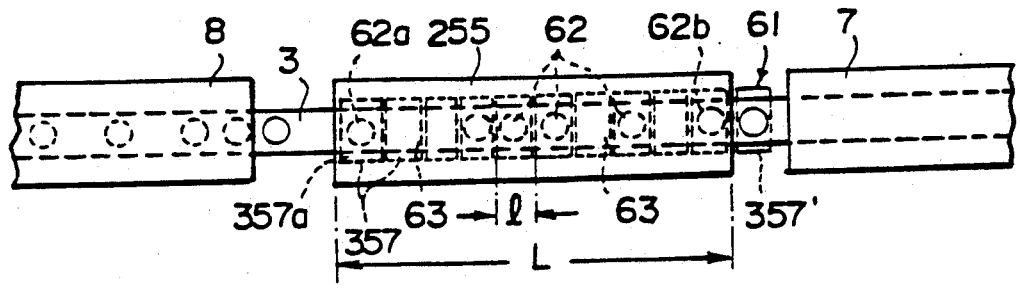
FIGS. 13A and 13B are explanatory views showing the condition of sample application onto a long test film in the embodiment shown in FIG. 12.
Figure 13B:
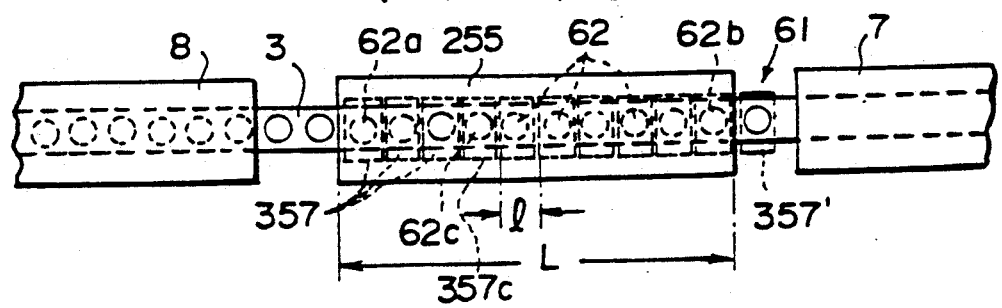

FIGS. 13A and 13B show the conditions of sample application onto the long test film 3.

FIG. 13A shows the case wherein a plurality of long test films 3, 3, . . . corresponding to a plurality of measurement items are provided side by side in the apparatus, and the long test film 3 shown is intermittently conveyed by a distance equal to the length l [cm] at one time with the predetermined period $\tau$ [min.] leftward even though measurement corresponding to the long test film 3 is not carried out. The predetermined period $\tau$ [min.] has the relationship of $\tau = 1/n$ with respect to n [number/min.].

The long test film 3 shown in FIG. 13A is conveyed leftward with the predetermined period of $\tau$ [min.] in the manner as mentioned above. A liquid sample is applied onto a portion of the long test film 3 pulled out of the film feed cassette 7 at the sample applying position 61, and then the sample-applied portion is conveyed into the incubator 255 and incubated.

A plurality of the measurement means 357, 357, . . . are provided to correspond to the respective sample-applied portions 62, 62, . . . , thereby to measure the optical density of a plurality of sample-applied portions 62, 62, . . . inside of the incubator 255. As mentioned above, a measurement means 357' may also be provided at the position for the measurement of the optical density at the sample applying position 61, thereby to measure the background, i.e. the optical density of the long test film 3 without the liquid sample applied thereon, at the sample applying position 61.

With the configuration of the apparatus wherein the long test film 3 is conveyed with the predetermined period of $\tau$ [min.] also when the measurement corresponding to the long test film 3 is not carried out as shown in FIG. 13A, measurement may be carried out, for example, with a measurement means 357a corresponding to the position 62a in the case where only the end point process for carrying out the measurement after the incubation has been carried out for the predetermined time is employed, instead of the rate process for measuring the optical density at a plurality of the sample-applied portions during the incubation. However, in this case, portions 63, 63, . . . of the long test film 3 remain unused, and the use efficiency of the long test film 3 decreases. On the other hand, in the case where the rate process is employed, it is necessary to provide a plurality of the measurement means 357, 357, . . . also when the apparatus is constituted to always convey the long test film 3 with the predetermined period $\tau$ [min.] as shown in FIG. 13A.

FIG. 13B shows an example wherein the apparatus is constituted to make the long test film 3 wait without conveying it in the case where the measurement corresponding to the long test film 3 is not carried out. In FIG. 13B, similar elements are numbered with the same reference numerals with respect to FIG. 13A. In this case, the long test film 3 may often wait for some time without being conveyed. Therefore, the predetermined incubation time may have already elapsed with the sample-applied portion being located at, for example, a position 62c also in the case where the end point process is employed. In this case, the optical density of the sample-applied portion at the position 62c is measured by a measurement means 357c corresponding to the position 62c.

With this embodiment wherein a plurality of the movement means 357, 357, . . . are provided, the measurement using the rate process can be carried out, and the use efficiency of the long test film 3 can be maximized by the utilization of the control method corresponding to FIG. 13B in both the end point process and the rate process.

Figure 14:
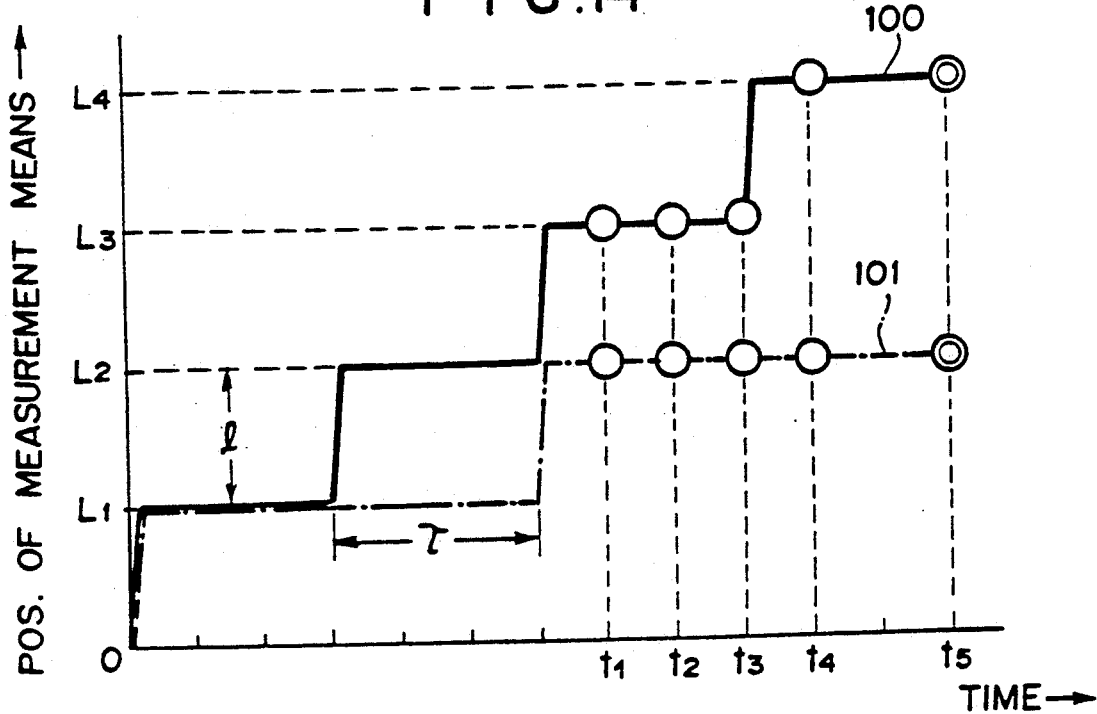
FIG. 14 is a graph showing an example of the relationship between the movement of a sample-applied portion and change-over of a plurality of measurement means.

FIG. 14 shows examples of the relationships between the movement of the sample-applied portion 62 in the incubator 255 and change-over of a plurality of the measurement means 357, 357, . . . shown in FIGS. 13A and 13B. The horizontal axis denotes the time as counted from when the sample-applied portion 62 has been accommodated in the incubator 255, and the vertical axis denotes the positions of a plurality of the measurement means 357, 357, . . . as measured from the edge of the incubator 255 on the side of the sample applying position 61 toward the opposite edge of the incubator 255. The single circle indicates the relationship between the time and the measurement means in the case where the measurement is carried out by use of the rate process, and the double circle indicates the relationship between the time and the measurement means in the case where the measurement is carried out by use of the end point process. In FIG. 10, for simplicity of explanation, it is assumed that only four sample-applied portions can be accommodated in the incubator 255, and the movement of only a single sample-applied portion is shown.

In FIG. 14, a graph 100 is for the case where the long test film 3 is conveyed by use of the control method illustrated in FIG. 13A. In the case where the end point process is employed, the measurement is carried out at the time t5 by the measurement means 357 provided at the position L4. In the case of the rate process, the optical density of a sample-applied portion is measured at the time t1, the time t2 and the time t3 by the measurement means 357 provided at the position L3. When the sample-applied portion is moved to the distance L4, the measurement is carried out at the time t4 by the measurement means 357 provided at the position L4. In this manner, the measurement means 357 used for the measurement is changed over in accordance with the movement of the sample-applied portion. In the case where a plurality of the sample-applied portions 62, 62, ... are simultaneously present inside of the incubator 255 and the measurement is carried out by the rate process, the measurement means 357, 357, ... are changed over to carry out the measurement for the respective sample-applied portions 62, 62, ... in the manner as mentioned above.

A graph 101 is for the case where the long test film 3 is conveyed by use of the control method illustrated in FIG. 13B. In this case, as indicated by the graph 101, the sample-applied portion 62 may be present at the distance L2 also at the time t5 for the measurement by the end point process. In this case, the optical density of the sample-applied portion 62 is measured by the measurement means 357 provided at the position L2. In the example of the graph 101, when the rate process is employed, measurement is carried out at the time t1, the time t2, the time t3 and the time t4 by the measurement means 357 provided at the position L2. When the control method corresponding to FIG. 13B is employed in this manner, the measurement is carried out by changing over the measurement means 357, 357, ... in both the rate process and the end point process.

Figure 15:
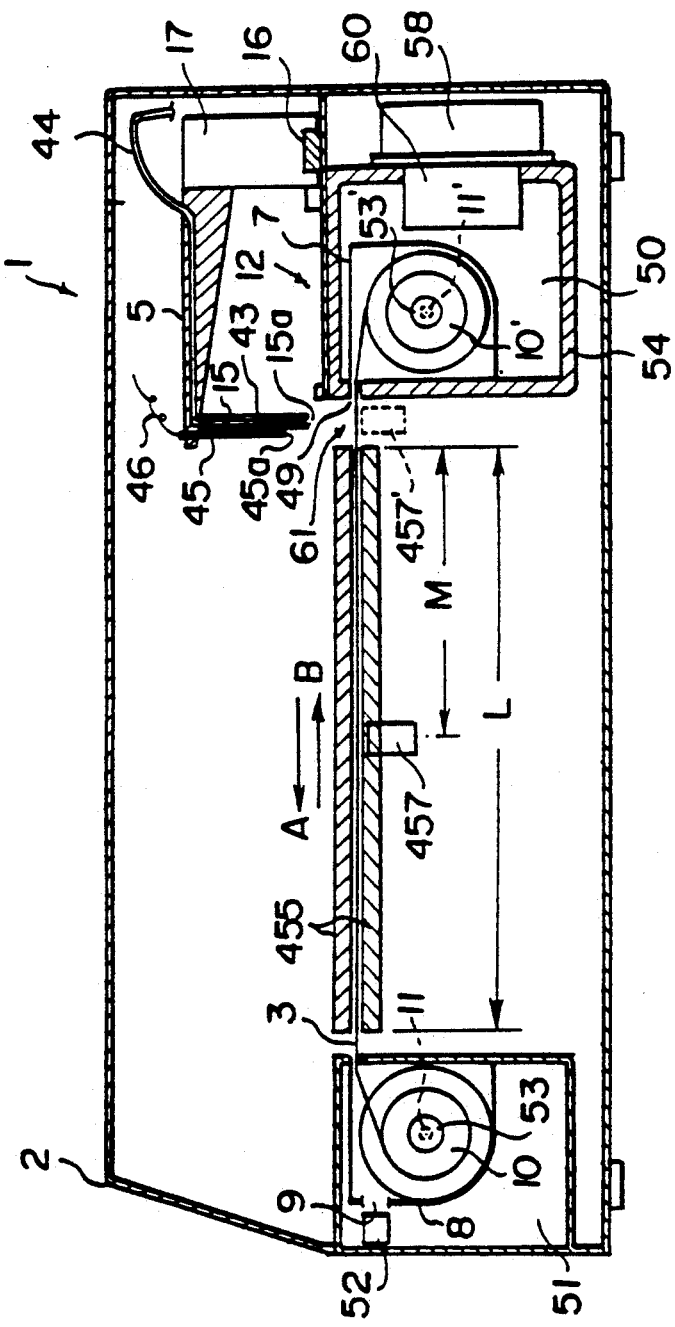
FIG. 15 is a sectional view taken along line X—X' of FIG. 2 and showing an embodiment of the fifth biochemical analysis apparatus in accordance with the present invention.

An embodiment of the fifth biochemical analysis apparatus in accordance with the present invention will hereinbelow be described with reference to FIGS. 15 and 16. In FIG. 15, similar elements are numbered with the same reference numerals with respect to FIG. 3.

With reference to FIG. 15, a hole 11' for engagement with the rotation shaft of a motor for rewinding the long test film 3, which has been pulled out of the film feed cassette 7, into the film feed cassette 7 is provided at the center of a reel 10' in the film feed cassette 7.

When the film wind-up cassette 8 and the film feed cassette 7 have been accommodated in the wind-up chamber 51 and the refrigerator 50 respectively, rotation shafts of the test film wind-up motor 53 and a test film rewinding motor 53' constituting the test film conveyance means engage with the hole 11 formed at the center of the reel 10 of the film wind-up cassette 8 and the hole 11' formed at the center of the reel 10' of the film feed cassette 7. As the motors 53 and 53' are rotated, the long test film 3 is continuously pulled out of the film feed cassette 7 through a film outlet 49 of the refrigerator 50, and is wound up in the film wind-up cassette 8. Also, when necessary, the long test film 3 pulled out of the film feed cassette 7 is rewound in the film feed cassette 7. The speed v [cm/min.] at which the long test film 3 is continuously pulled out of the film feed cassette 7 is expressed as $$v = n \cdot l$$

where l [cm] denotes the length of a portion of the long test film 3 necessary for a single step of sample application, and n [number/min.] denotes the number of repetitions of the sample application per minute.

The length L [cm] of the incubator 455 in the direction of conveyance of the long test film 3 is defined as described below.

First, in this embodiment, the incubation time t [min.] is defined as the time from when the overall portion having the length l [cm] on which a liquid sample has been applied in a single step of sample application is conveyed into the incubator (i.e. the origin in FIG. 8) to when the portion having the length l [cm] is at least partially conveyed out of the incubator (i.e. the point t0 in FIG. 8), i.e. the time for which the overall portion having the length l [cm] is accommodated in the incubator. This is because it is a mere matter of definition whether the time for which the overall portion having the length l [cm] is accommodated in the incubator is referred to as the incubation time or whether the time for which the portion having the length l [cm] is at least partially accommodated in the incubator is referred to as the incubation time. In the case where the definition is changed, the formulas expressed for this embodiment are changed in accordance with the change in the definition.

All of the sample-applied portions can be accommodated over a length L" in the incubator 455 in the case where the incubator 455 has the length L" [cm] expressed as $$L' \geqq v \cdot t + l \tag{22}$$

where l [cm] denotes the length of a portion of the long test film 3 necessary for a single step of sample application, t [min.] denotes the time for which the sample-applied portion of the long test film 3 is to be maintained at a predetermined temperature inside of the incubator 455, n [number/min.] denotes the number of repetitions of the sample application per unit time, and v [cm/min.] denotes the wind-up speed at which the long test film 3 is continuously wound up by the wind-up motor 53. In this embodiment, the wind-up speed is equal to the speed at which the long test film 3 is pulled out of the film feed cassette 7, and the speed of conveyance of the pulled-out long test film 3 inside of the incubator 455. As mentioned above, the formula $$v = n \cdot l \tag{23}$$

applies. Substitution of Formula (23) into Formula (22) yields $$L'' \geqq (nt + 1) \cdot l \tag{24}$$

Therefore, in the case where the incubator 455 has a length satisfying the condition of $L'' \geqq (nt+1) \cdot l$ and a measurement means 457 is provided at a position of $M = (nt+1) \cdot l$, the optical density of the sample-applied portion after being incubated for the predetermined time t [min.] can be measured by the measurement means 457 in accordance with the end point process.

In the case where the optical density is measured by the rate process, the measurement must be carried out before the sample-applied portion is incubated for the predetermined time t [min.]. Therefore, the long test film 3 is conveyed by the motors 53 and 53' toward the film wind-up cassette 8 until a predetermined sample-applied portion of the long test film 3 is brought to the position corresponding to the measurement means 457. In this case, sample-applied portions on which a liquid sample has been applied prior to said predetermined sample-applied portion and which are to be measured must be maintained in the incubator 455 and continue to be incubated. For this purpose, the incubator 455 should have the length L" expressed as Formula (24) also on the side closer to the wind-up chamber 51 than the measurement means 457. Therefore, the length L [cm] of the incubator 455 in the direction of conveyance of the long test film 3 is defined as $$L \geqq 2 \cdot L'' \geqq 2l \cdot (nt + 1) \tag{25}$$

The distance M [cm] between an inlet of the incubator 455 for the long test film 3 and the measurement means 457 as measured from the inlet toward an outlet of the incubator 455 is defined as described below.

In order that all of the portions of the long test film 3 on which the liquid sample has been applied sequentially be accommodated in the area of the incubator 455 on the side closer to the film feed cassette 7 than the measurement means 457, the measurement means 457 should be provided at a position satisfying the condition $$M \geq (nt+1) \cdot l \qquad (26)$$

Also, in order that all of the sample-applied portions be accommodated in the area of the incubator 455 on the side closer to the film wind-up cassette 8 than the measurement means 457, the measurement means 457 should be provided at a position satisfying the condition $$M \leq L - (nt+1) \cdot l \qquad (27)$$

The distance M [cm] satisfying Formula (26) and Formula (27) at the same time is expressed as $$L - (nt+1) \cdot l \leq M \leq (nt+1) \cdot l \qquad (28)$$

In this embodiment wherein the test film conveyance means is constituted by the motors 53 and 53', the long test film 3 is continuously moveable reciprocally, the incubator 455 has the length satisfying the condition of Formula (25) and the measurement means 457 is provided at the position satisfying the condition of Formula (28), measurement can be carried out also by use of the rate process, and the sample application, incubation and measurement can be carried out quickly and sequentially.

Since the measurement is carried out by moving the long test film 3 as mentioned above, a plurality of the sample-applied portions cannot be measured simultaneously. However, in the end point process, measurement may be carried out sequentially with the same period as the period of sequential sample application, and therefore a plurality of the sample-applied portions need not be simultaneously measured. On the other hand, in the rate process, even though a plurality of the sample-applied portions cannot be measured simultaneously, the change caused by a color formation progresses temporally continuously, and therefore the measured values can be corrected as the time at which the measurement is carried out deviates slightly.

A measurement means 457' may also be provided to measure the background, i.e. the optical density of the long test film 3 without the liquid sample applied thereon, at the sample applying position 61. The value measured by the measurement means 457 after the sample application and incubation have been carried out may be corrected based on the measured background density. In this manner, the measurement accuracy can be improved.

Figure 16:
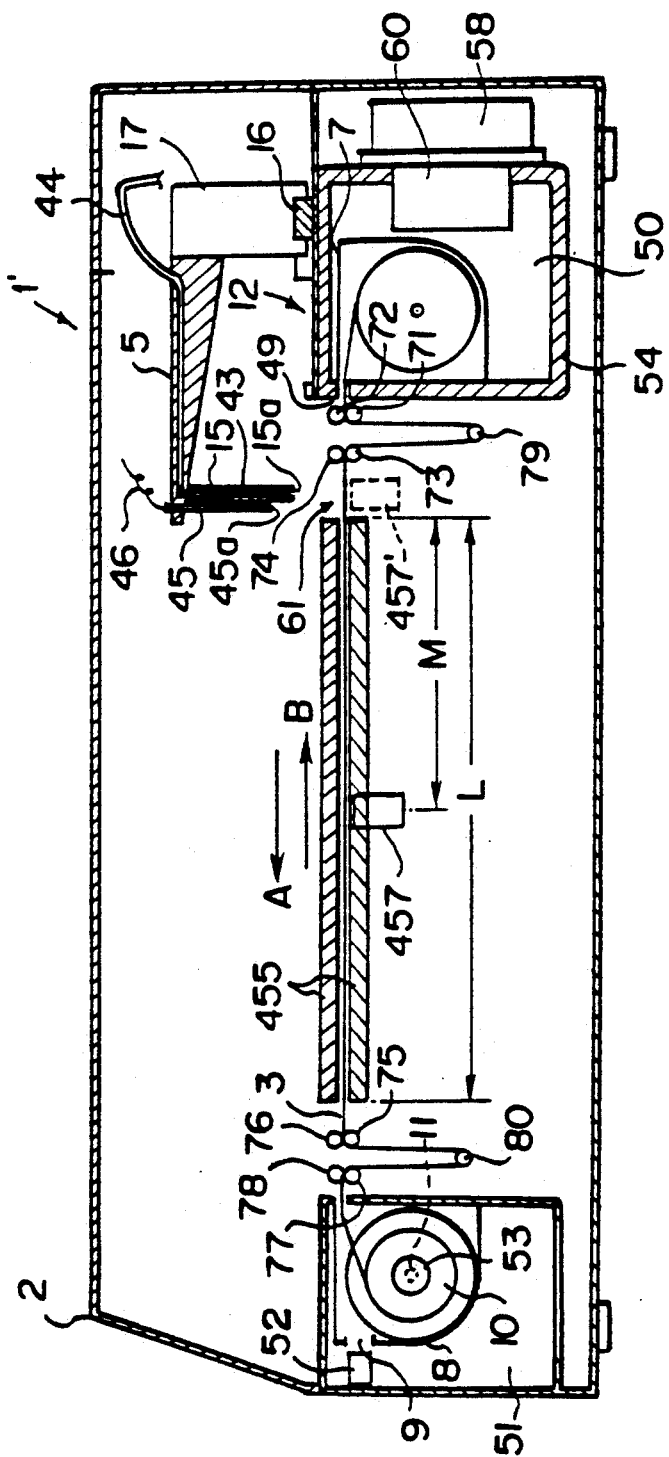
FIG. 16 is a sectional view showing another embodiment of the fifth biochemical analysis apparatus in accordance with the present invention.

FIG. 16 shows another embodiment of the fifth biochemical analysis apparatus in accordance with the present invention. In FIG. 16, similar elements are numbered with the same reference numerals with respect to FIG. 15.

With reference to FIG. 16, the exposed portion of the long test film 3 between the film feed cassette 7 and the film wind-up cassette 8 passes between rollers 71 and 72, applied around a gravity roller 79, passes between rollers 73 and 74, and then passes through the incubator 455. After leaving the incubator 455, the long test film 3 passes between rollers 75 and 76, applied around a gravity roller 80, and passes between rollers 77 and 78. The roller 71 is coupled with a rotation shaft of a motor (not shown). On the other hand, no motor is provided for the film feed cassette 7. The motor is rotated in the direction that pulls out the long test film 3 from the film feed cassette 7, and is controlled so that the height of the gravity roller 79 is within a predetermined range.

The roller 75 is coupled with a rotation shaft of a motor (not shown) capable of being rotated in normal and reverse directions. The rollers 75 and 73 are coupled to simultaneously convey the long test film 3 by the same distances in the same direction. The motor is rotated in the normal or reverse direction to convey a predetermined sample-applied portion of the long test film 3 to the position corresponding to the measurement means 457. When a part of the long test film 3 is conveyed out of the incubator 455 by this conveyance operation, one of the gravity rollers 79 and 80 is moved down and the other thereof is moved up, and said part of the long test film 3 is temporarily accommodated at the position of the gravity roller moved down.

A portion of the long test film 3 at which the measurement has been finished is wound up in the film wind-up cassette 8 by the motor 53 engaging with the hole 11 provided at the center of the reel 10 of the film wind-up cassette 8.

The long test film 3 may be provided so that the part inside of the incubator 455 is moveable reciprocally as in this embodiment, and the overall long test film 3 need not necessarily be moved reciprocally.

An embodiment of the sixth biochemical analysis apparatus in accordance with the present invention will hereinbelow be described with reference to FIG. 3. In this embodiment, the long test film 3 is intermittently pulled out of the film feed cassette 7 by a distance equal to the length l [cm] of the long test film 3 necessary for a single step of sample application through the outlet 49 of the refrigerator 50.

In this embodiment, the length L [cm] of the incubator 55 in the direction of conveyance of the long test film 3 is defined as described below. Specifically, the incubator 55 has the length L [cm] expressed as $$L \geq [nt+1] \cdot l \qquad (29)$$

where l [cm] denotes the length of a portion of the long test film 3 necessary for a single step of sample application, t [min.] denotes the time for which the sample-applied portion of the long test film 3 is to be maintained at a predetermined temperature inside of the incubator 55, and n [number/min.] denotes the number of repetitions of the sample application per unit time. Also, [nt+1] denotes the largest integer within the range not larger than nt+1.

In the case where the incubator 55 has the length expressed by L, the processing capacity of the apparatus 1 does not decrease even though a long time t [min.] is taken for the incubation.

FIG. 8 shows the relationship between the necessary incubation time t [min.] and the necessary length L (i.e. L') [cm] of the incubator 55. The long test film 3 is intermittently conveyed by a distance equal to the length l [cm] necessary for a single step of sample application. In FIG. 8, the rightwardly-rising, step-like, hatched region indicates the temporal movement condition of the portion (length l [cm]) of the long test film, on which the liquid sample has been applied in a single step, in the incubator. A period $\tau$ [min.] of the intermittent conveyance of the long test film is expressed as $$\tau = \tau 1 + \tau 2 \tag{30}$$

where $\tau 1$ [min.] denotes each stop time for which the long test film 3 is stopped in the intermittent conveyance, and $\tau 2$ [min.] denotes each movement time between the start of the movement of the long test film 3 after the stop time $\tau 1$ [min.] has elapsed and the stop at the next stop position after the movement by a distance equal to the length l [cm]. Therefore, the number n [number/min.] of repetitions of the sample application per minute is expressed as $$n = \frac{1}{\tau_1 + \tau_2} = \frac{1}{\tau} \tag{31}$$

The incubation time t [min.] is defined as described below. The time at which the overall sample-applied portion having the length l [cm] is conveyed into the incubator is taken as the origin. The time elapsed between the origin and the point t0 at the end of the last stop time $\tau 1$ [min.] after the stop-movement cycle has been repeated several times is taken as the incubation time t [min.]. It is a mere matter of definition whether the time for which the overall portion having the length l [cm] is accommodated in the incubator is referred to as the incubation time or whether the time for which the portion having the length l [cm] is at least partially accommodated in the incubator is referred to as the incubation time. Therefore, in this embodiment, the time for which overall sample-applied portion having the length l [cm] is being accommodated in the incubator is defined as the incubation time t [min.]. Also, the color forming reaction caused by the incubation is continuous, and therefore the measured value can be corrected when the time between the start of the incubation and the measurement of the optical density caused by the color forming reaction changes slightly. Therefore, generality is not lost in the case where the time at which the overall sample-applied portion having the length l [cm] is accommodated in the incubator is taken as the origin, and the time t [min.] elapsed between the origin and the point t0 at the end of the last stop time $\tau 1$ [min.] after the stop-movement cycle has been repeated several times is taken as the incubation time. In the case where the definition is changed, the formulas expressed for this embodiment are changed in accordance with the change in the definition. In the case where the long test film is conveyed continuously so that the conveyance speed v [cm/min.] is expressed as $$v = \frac{l}{\tau} = n \cdot l \tag{32}$$

as indicated by the rightwardly-rising, parallel straight lines in FIG. 8, in order that the overall sample-applied portion having the length l [cm] is accommodated in the incubator for the incubation time t [min.], the length L″ [cm] of the incubator should satisfy the condition $$L'' \geq v \cdot t + l = (nt+1) \cdot l \tag{33}$$

However, in this embodiment, the long test film is conveyed intermittently so that it stops for the time $\tau 1$ [min.] and moves for the time $\tau 2$ [min.]. Therefore, the necessary length L (i.e. L') [cm] of the incubator should satisfy the condition $$L \geq [nt+1] \cdot l \tag{34}$$

where nt+1] denotes the largest integer within the range not larger than nt+1.

In order to define the length L of the incubator 55, it is only necessary that the part of the long test film 3 inside of the incubator 55 is conveyed intermittently by a distance equal to the length l [cm] at one time. For example, the long test film 3 may be continuously pulled out of the film feed cassette 7, and a buffer for shifting the conveyance of the long test film 3 from continuous operation to the intermittent operation may be provided between the refrigerator 50 and the sample applying position 61.

As mentioned above, in this embodiment, the biochemical analysis apparatus 1 is constituted to simultaneously accommodate a plurality of the long test films 3, 3, ... The incubation time t [min.] often differs among the long test films 3, 3, ... for use in analysis of different chemical ingredients or the like. In this case, the length of the incubator 55 should preferably be adjusted to be equal to the length corresponding to the longest incubation time, so that a long test film 3 requiring a long incubation time may be accommodated at any position in the test film accommodating means 12. Also, in the case of a single-function type apparatus capable of accommodating only a single long test film 3, the length L [cm] of the incubator 55 is adjusted in accordance with a long test film 3 requiring the longest incubation time t [min.] among a plurality of the long test films 3, 3, ... which are expected to be used in the apparatus.

The sixth biochemical analysis apparatus in accordance with the present invention may also be constituted as shown in FIG. 4. Also, in this case, the length L [cm] of the incubator 55' is defined in the same manner as in the first embodiment of the sixth biochemical analysis apparatus in accordance with the present invention.

An embodiment of the seventh biochemical analysis apparatus in accordance with the present invention will hereinbelow be described with reference to FIG. 3. In this embodiment, the long test film 3 is intermittently pulled out of the film feed cassette 7 by a distance equal to the length l [cm] of the long test film 3 necessary for a single step of sample application through the outlet 49 of the refrigerator 50.

In this embodiment, the length L [cm] of the incubator 55 in the direction of conveyance of the long test film 3 is defined by Formula (29) as in the sixth biochemical analysis apparatus in accordance with the present invention.

Also, the measurement by the end point process can be carried out by providing the measurement means 57 at a position of $$M = [nt+1] \cdot l \tag{35}$$

where l [cm] denotes the length of a portion of the long test film 3 necessary for a single step of sample application, and t [min.] denotes the time for which the sample-applied portion of the long test film 3 is to be maintained at a predetermined temperature inside of the incubator 55.

In the case where the incubator 55 has the length expressed by L, the processing capacity of the apparatus 1 does not decrease even though a long time t [min.] is taken for the incubation. Also, as the measurement means 57 is provided at the position indicated by M in Formula (35), the measurement using the end point process can be carried out continuously by measuring the optical density of the sample-applied portion of the long test film 3 at the end of the incubation time t for said sample-applied portion.

Also, with this embodiment wherein the end point process is employed, the measurement means 57 may be located at the position capable of measuring the sample-applied portion of the long test film 3 exactly after the incubation time t [min.] has elapsed. Therefore, the distance M [cm] between the inlet of the incubator 55 for the long test film 3 and the measurement means 57 as measured from the inlet to the outlet of the incubator should satisfy the condition $$M = [nt+1] \cdot l \qquad (36)$$

In order to define the length L of the incubator 55 and the position of the measurement means 57, it is only necessary that only the part of the long test film 3 inside of the incubator 55 be conveyed intermittently by a distance equal to the length l [cm] at one time. For example, the long test film 3 may be continuously pulled out of the film feed cassette 7, and a buffer for shifting the conveyance of the long test film 3 from the continuous operation to the intermittent operation may be provided between the refrigerator 50 and the sample applying position 61.

As mentioned above, in this embodiment, the biochemical analysis apparatus 1 is constituted to simultaneously accommodate a plurality of the long test films 3, 3, . . . The incubation time t [min.] often differs among the long test films 3, 3, . . . for use in analysis of different chemical ingredients or the like. In this case, the length of the incubator 55 should preferably be adjusted to be equal to the length corresponding to the longest incubation time, so that a long test film 3 requiring a long incubation time may be accommodated at any position in the test film accommodating means 12. In this case, the measurement means 57 is manually or automatically moved to the position corresponding to the incubation time for the accommodated long test film 3. Also, in the case of a single-function type apparatus capable of accommodating only a single long test film 3, the length L [cm] of the incubator 55 is adjusted in accordance with a long test film 3 requiring the longest incubation time t [min.] among a plurality of the long test films 3, 3, . . . which are expected to be used in the apparatus, and the measurement means 57 is manually or automatically moved to the position corresponding to the incubation time for the accommodated long test film 3.

The seventh biochemical analysis apparatus in accordance with the present invention may also be constituted as shown in FIG. 4. Also, in this case, the length L [cm] of the incubator 55' and the position M [cm] of the measurement means 57 are defined in the same manner as in the first embodiment of the seventh biochemical analysis apparatus in accordance with the present invention.

An embodiment of the eighth biochemical analysis apparatus in accordance with the present invention will hereinbelow be described with reference to FIGS. 15, 16, 17A and 17B.

With reference to FIG. 15, in this embodiment, the long test film 3 is intermittently pulled out of the film feed cassette 7 by a distance equal to the length l [cm] of the long test film 3 necessary for a single step of sample application at intervals of, for example, the time 1/n [min.] necessary for a single step of sample application, through the outlet 49 of the refrigerator 50. Also, when necessary, the long test film 3 pulled out of the film feed cassette 7 is rewound in the film feed cassette 7.

In this embodiment, the length L [cm] of the incubator 455 in the direction of conveyance of the long test film 3 is defined as described below. As mentioned above by use of Formulas (30) to (34) with reference to FIG. 8 showing the embodiment of the sixth biochemical analysis apparatus in accordance with the present invention, the long test film is conveyed intermittently so that it stops for the time $\tau 1$ [min.] and moves for the time $\tau 2$ [min.]. Therefore, the necessary length L' [cm] of the incubator should satisfy the condition $$L' \geq [nt+1] \cdot l \qquad (37)$$

where [nt+1] denotes the largest integer within the range not larger than nt+1.

Therefore, in the case where the incubator 455 has a length satisfying the condition of $L' \geq [nt+1] \cdot l$ and the measurement means 457 is provided at a position of $M = [nt+1] \cdot l$, all of the sample-applied portions of the long test film 3 can be accommodated in the incubator 455, and the optical density of the sample-applied portion after being incubated for the predetermined time t [min.] can be measured by the measurement means 457 in accordance with the end point process.

In the case where the optical density is measured by the rate process, the measurement must be carried out before the sample-applied portion is incubated for the predetermined time t [min.]. Therefore, the long test film 3 is conveyed by the motors 53 and 53' toward the film wind-up cassette 8 until a predetermined sample-applied portion of the long test film 3 is brought to the position corresponding to the measurement means 457. In this case, sample-applied portions on which a liquid sample has been applied prior to said predetermined sample-applied portion and which are to be measured must be maintained in the incubator 455 and continue to be incubated. For this purpose, the incubator 455 should have the length L' expressed as Formula (37) also on the side closer to the wind-up chamber 51 than the measurement means 457. Therefore, the length L [cm] of the incubator 455 in the direction of conveyance of the long test film 3 is defined as $$L \geq 2 \cdot L' \geq 2l \cdot [nt+1] \qquad (38)$$

In this embodiment of the eighth biochemical analysis apparatus in accordance with the present invention, the distance M [cm] between an inlet of the incubator 455 for the long test film 3 and the measurement means 457 as measured from the inlet toward an outlet of the incubator 455 is defined as described below.

In order that all of the portions of the long test film 3 on which the liquid sample has been applied sequentially be accommodated in the area of the incubator 455 on the side closer to the film feed cassette 7 than the measurement means 457, the measurement means 457 should be provided at a position satisfying the condition $$M \geq [nt+1] \cdot l \qquad (39)$$

Also, in order that all of the sample-applied portions be accommodated in the area of the incubator 455 on the side closer to the film wind-up cassette 8 than the measurement means 457, the measurement means 457 should be provided at a position satisfying the condition $$M \leq L - [nt+1] \cdot l \tag{40}$$

The distance M [cm] satisfying Formula (39) and Formula (40) at the same time is expressed as $$L - [nt+1] \cdot l \leq M \leq [nt+1] \cdot l \tag{41}$$

In this embodiment wherein the test film conveyance means is constituted by the motors 53 and 53', the long test film 3 is moveable reciprocally, the incubator 455 has the length satisfying the condition of Formula (38) and the measurement means 457 is provided at the position satisfying the condition of Formula (41), measurement can be carried out also by use of the rate process, and the sample application, incubation and measurement can be carried out quickly and sequentially.

Since the measurement is carried out by moving the long test film 3 as mentioned above, a plurality of the sample-applied portions cannot be measured simultaneously. However, in the end point process, measurement may be carried out sequentially with the same period as the period of sequential sample application, and therefore a plurality of the sample-applied portions need not be simultaneously measured. On the other hand, in the rate process, even though a plurality of the sample-applied portions cannot be measured simultaneously, the change caused by a color formation progresses temporally continuously, and therefore the measured values can be corrected as the time at which the measurement is carried out deviates slightly.

Also, in this embodiment, the measurement means 457' may be provided to measure the background, i.e. the optical density of the long test film 3 without the liquid sample applied thereon, at the sample applying position 61. The value measured by the measurement means 457 after the sample application and incubation have been carried out may be corrected based on the measured background density. In this manner, the measurement accuracy can be improved.

Figure 17A:
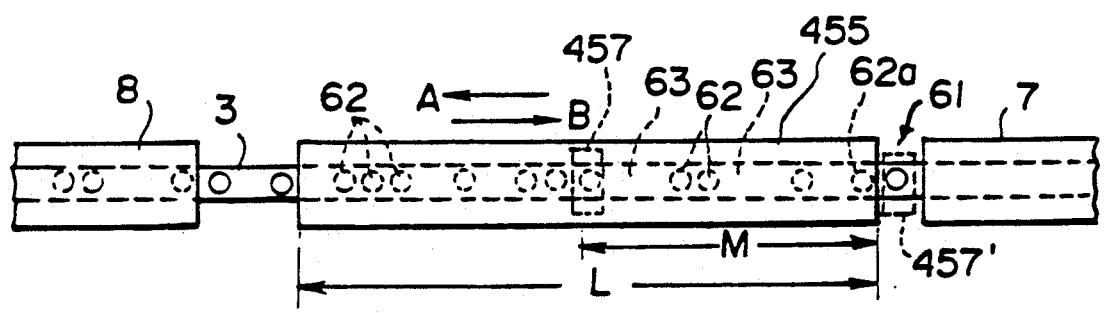
FIGS. 17A and 17B are explanatory views showing the condition of sample application onto a long test film in an embodiment of the eighth embodiment of the biochemical analysis apparatus in accordance with the present invention.
Figure 17B:
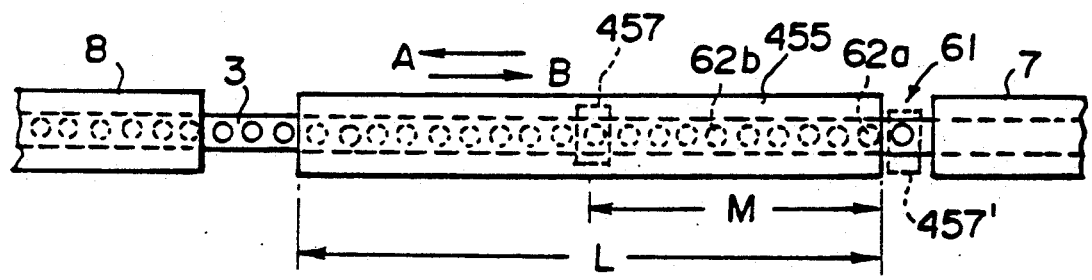

FIGS. 17A and 17B show the conditions of sample application onto the long test film 3.

FIG. 17A shows the case wherein a plurality of long test films 3, 3, ... corresponding to a plurality of measurement items are provided side by side in the apparatus, and the long test film 3 shown is intermittently conveyed by a distance equal to the length l [cm] at one time with the predetermined period τ [min.] leftward even though measurement corresponding to the long test film 3 is not carried out. The predetermined period τ [min.] has the relationship of τ = 1/n with respect to n [number/min.].

The long test film 3 shown in FIG. 17A is conveyed leftward with the predetermined period of τ [min.] in the manner as mentioned above. A liquid sample is applied onto a portion of the long test film 3 pulled out of the film feed cassette 7 at the sample applying position 61, and then the sample-applied portion is conveyed into the incubator 455 and incubated.

As mentioned above, the length L of the incubator 455 satisfies the condition of L ≧ 2l·[nt+1], and the distance M between the inlet of the incubator 455 and the measurement means 457 is within the range of L−l·[nt+1] ≦ M ≦ l·[nt+1]. The long test film 3 is reciprocally conveyed by the test film conveyance means in the directions as indicated by the arrows A and B, a predetermined sample-applied portion among a plurality of the sample-applied portions 62, 62, ... is moved to the position corresponding to the measurement means 457, and the optical density of said sample-applied portion is measured.

Also, as mentioned above, the measurement means 457' may be provided for the measurement of the optical density at the sample applying position 61, thereby to measure the background, i.e. the optical density of the long test film 3 without the liquid sample applied thereon, at the sample applying position 61.

With the configuration of the apparatus wherein the long test film 3 is conveyed with the predetermined period of τ [min.] also when the measurement corresponding to the long test film 3 is not carried out as shown in FIG. 17A, measurement can be carried out sequentially by the measurement means 457 by sequentially conveying the long test film 3 only toward the film wind-up cassette 8 in the case where only the end point process for carrying out the measurement after the incubation has been carried out for the predetermined time is employed, instead of the rate process for measuring the optical density at a plurality of the sample-applied portions during the incubation. However, in this case, portions 63, 63, ... of the long test film 3 remain unused, and the use efficiency of the long test film 3 decreases. On the other hand, when the rate process is employed, it is necessary for the long test film 3 to be moved reciprocally also in the case of FIG. 17A. In this case, each time a single step of measurement is finished, the latest sample-applied portion 62 (including the unused portion 63 on which no liquid sample has been applied because of the conveyance) on the long test film 3 is moved to the position 62a closest to the inlet of the incubator 455, and waits at the position 62a. In the case where the liquid sample is applied to a new portion of the long test film 3 at the sample applying position 61 or in the case where the predetermined period τ [min.] has elapsed without sample application when the measurement corresponding to the long test film 3 is not to be carried out, the long test film 3 is conveyed by the test film conveyance means by a distance equal to the length l [cm] toward the film wind-up cassette 8, and waits for the next step. In the case where the measurement of a predetermined sample-applied portion becomes necessary during this operation, the predetermined sample-applied portion is moved to the position corresponding to the measurement means 457, subjected to the measurement, and then the long test film 3 is returned to the waiting condition.

FIG. 17B shows an example wherein the apparatus is constituted to make the long test film 3 wait without conveying it in the case where the measurement corresponding to the long test film 3 is not carried out. In FIG. 17B, similar elements are numbered with the same reference numerals with respect to FIG. 17A. In this case, the long test film 3 may often wait for some time without being conveyed. Therefore, the predetermined incubation time may have already elapsed with the sample-applied portion being located at, for example, a position 62b also in the case where the end point process is employed. In this case, the the sample-applied portion at the position 62b is moved to the position corresponding to the measurement means 457 and subjected to the measurement.

As in the case of FIG. 17A, after the predetermined sample-applied portion is moved to the position corresponding to the measurement means 457 and subjected to the measurement, the long test film 3 is moved until the latest sample-applied portion is located at the position 62a, and is then returned to the waiting condition. However, in FIG. 17B, in the case where a new step of sample application is not carried out at the sample applying position 61 as the measurement corresponding to the long test film 3 is not to be carried out, the long test film 3 is maintained in the current waiting condition without being conveyed.

With this embodiment wherein the long test film 3 is moveable reciprocally, the measurement using the rate process can be carried out, and the use efficiency of the long test film 3 can be maximized by the utilization of the control method corresponding to FIG. 17B in both the end point process and the rate process.

The eighth biochemical analysis apparatus in accordance with the present invention may also be constituted as shown in FIG. 16.

We claim:

1. A biochemical analysis apparatus comprising:
   i) a sample accommodating means for containing a liquid sample,
   ii) a test film having a continuous length and containing a reagent which reacts with said liquid sample to give rise to a change in optical density of said test film,
   iii) a test film accommodating means for storing said test film having a continuous length and containing a reagent which reacts with said liquid sample to give rise to a change in optical density of said test film,
   iv) a test film conveyance means for sequentially pulling out said test film stored in said test film accommodating means and then conveying said test film,
   v) a sample application means for taking up said liquid sample contained in said sample accommodating means and applying a predetermined amount of said liquid sample onto said test film at the position to which said test film has been pulled out from said test film accommodating means and conveyed,
   vi) an incubator for maintaining the sample-applied portion of said test film at a predetermined temperature for a predetermined time, said incubator being positioned between said sample application means and said test film conveyance means, and
   vii) a measurement means for irradiating light to said sample-applied portion of said test film and measuring the change in said optical density of said test film given rise to by said reaction during or after the passage of said predetermined time, said measurement means being reciprocally movable between said position at which said test film has a sample applied thereto and a second position at an end of said incubator;
   wherein:
   a) said test film conveyance means includes means to continuously convey at least a part of said test film inside of said incubator so that a speed v (cm/min.) at which the part of said test film inside of said incubator is continuously conveyed is expressed as $v = n \cdot l,$ and b) said incubator has a length L (cm) in the direction of conveyance of said test film which satisfies the condition $L \geq (nt+1) \cdot l,$ where l (cm) denotes the length of a portion of said test film necessary for a single step of sample application, t (min.) denotes said predetermined time, and n (number/min.) denotes the number of repetitions of one of said sample application per unit time.

2. A biochemical analysis apparatus comprising:
   i) a sample accommodating means for containing a liquid sample,
   ii) a test film having a continuous length and containing a reagent which reacts with said liquid sample to give rise to a change in optical density of said test film,
   iii) a test film accommodating means for storing said test film having a continuous length and containing a regent which reacts with said liquid sample to give rise to a change in optical density of said test film,
   iv) a test film conveyance means for sequentially pulling out said test film stored in said test film accommodating means and then conveying said test film,
   v) a sample application means for taking up said liquid sample contained in said sample accommodating means and applying a predetermined amount of said liquid sample onto said test film at the position to which said test film has been pulled out from said test film accommodating means and conveyed,
   vi) an incubator for maintaining the sample-applied portion of said test film at a predetermined temperature for a predetermined time, said incubator being positioned between said sample application means and said test film conveyance means, and
   vii) a measurement means for irradiating light to said sample-applied portion of said test film and measuring the change in said optical density of said test film given rise to by said reaction after the passage of said predetermined time, said measurement means being reciprocally movable between said position at which said test film has a sample applied thereto and a second position at an end of said incubator;
   wherein:
   a) said test film conveyance means includes means to continuously convey at least a part of said test film inside of said incubator so that a speed v (cm/min.) at which the part of said test film inside of said incubator is continuously conveyed is expressed as $v = n \cdot l,$ said incubator has a length L (cm) in the direction of conveyance of said test film which satisfies the condition $L \geq (nt+1) \cdot l,$ and c) a distance M (cm) between an inlet of said incubator for said test film and said measurement means as measured from said inlet of said incubator toward an outlet thereof satisfies the condition $$M = (nt+1) \cdot l,$$

where l (cm) denotes the length of a portion of said test film necessary for a single step of sample application, t (min.) denotes said predetermined time, and n (number/min.) denotes the number of repetitions of one of said sample application per unit time.

* * * * *